US008298789B2

(12) United States Patent
Sankararaman et al.

(10) Patent No.: US 8,298,789 B2

(45) Date of Patent: Oct. 30, 2012

(54) ORTHOGONAL PROCESS FOR PURIFICATION OF RECOMBINANT HUMAN PARATHYROID HORMONE (RHPTH) (1-34)

(75) Inventors: Uma Sankararaman, Navi Mumbai (IN); Dipanwita Maiti, Mumbai (IN); Meera Sankarankutty, Mumbai (IN); Rakesh Shekhawat, Dombivali(E) (IN); Narasimha Kumar Kopparapu, Andhra Pradesh (IN); Gulnaz Zaidi, Maharshtra (IN); Bipinchandra Rathod, Mumbai (IN); Niren Praful Thakar, Mumbai (IN); Priti Thakur, Mumbai (IN); Anjali Chutke, Mumbai (IN); Shrikant Mishra, Mumbai (IN)

(73) Assignee: USV Limited, Govandi Mumbai, Maharashtra (IN)

( * ) Notice: Subject to any disclaimer, the term of this patent is extended or adjusted under 35 U.S.C. 154(b) by 142 days.

(21) Appl. No.: 12/452,919

(22) PCT Filed: Dec. 6, 2007

(86) PCT No.: PCT/IN2007/000573

§ 371 (c)(1), (2), (4) Date: Jan. 28, 2010

(87) PCT Pub. No.: WO2009/019715

PCT Pub. Date: Feb. 12, 2009

(65) Prior Publication Data

US 2010/0145033 A1 Jun. 10, 2010

(30) Foreign Application Priority Data

Aug. 9, 2007 (IN) ........................ 1543/MUM/2007

(51) Int. Cl.
*C12N 15/16* (2006.01)

(52) U.S. Cl. ...................................... 435/69.4; 435/71.2

(58) Field of Classification Search ................. 435/69.4, 435/71.2

See application file for complete search history.

(56) References Cited

U.S. PATENT DOCUMENTS

| | | | |
|---|---|---|---|
| 4,086,196 | A | 4/1978 | Tregear |
| 5,208,041 | A | 5/1993 | Sindrey |
| 5,457,047 | A | 10/1995 | Wingender et al. |
| 5,496,801 | A | 3/1996 | Holthuis |
| 5,670,340 | A | 9/1997 | Yabuta et al. |
| 6,590,081 | B1 | 7/2003 | Zhang |

FOREIGN PATENT DOCUMENTS

| | | | |
|---|---|---|---|
| CN | 1311256 | A | 9/2001 |
| CN | 1807456 | A | 7/2006 |
| EP | 0483509 | B1 | 7/1995 |
| WO | WO-99/05277 | A1 | 2/1999 |
| WO | WO-03/100022 | A2 | 12/2003 |

OTHER PUBLICATIONS

Neubauer et al.; Maximizing the expression of a recombinant gene in *Escherichia coli* by manipulation of induction time using lactose as inducer; Applied Microbiology and Biotechnology; vol. 36; pp. 739-744 (1992).*

Novagen pET system manual; 10th edition, published May 2003.*

"International Application Serial No. PCT/IN2007/000573, International Search Report mailed Oct. 27, 2008", 3 pgs.

Gagnon, P., "The Secrets of Orthogonal Process Design", *Validated Biosystems—Resource Guide for Downstream Processing*, [online]. [retrieved Oct. 8, 2008]. Retrieved from the internet: <URL: http://www.validated.com/revalbio/pdffiles/orthopd.pdf>, (Jul. 30, 2006), 4 pgs.

Gardella, T. J., et al., "Expression of Human Parathyroid Hormone-(1-84) in *Escherichia coli* as a Factor X-cleavable Fusion Protein", *The Journal of Biological Chemistry*, 265(26), 1990, 15854-15859.

Jin, L., et al., "Crystal Structure of Human Parathyroid Hormonee 1-34 at 0.9-Å Resolution", *The Journal of Biological Chemistry*, 275(35), 2000 , 27238-27244.

Pellegrini, M., et al., "Addressing the Tertiary Structure of Human Parathyroid Hormone-(1-34)", *The Journal of Biological Chemistry*, 273(17), (1998), 10420-10427.

Potts, J. T., et al., "Synthesis of a Biologically Active N-Terminal Tetratriacontapeptide of Parathyroid Hormone", *Proceedings of the National Academy of Sciences*, 68(1), (1971), 63-67.

Shen, S.-H., "Multiple joined genes prevent product degradation in *Escherichia coll", Proc. Natl Acad Sci USA.*, 81(15), Aug. 1984), 4627-4631.

Suzuki, Y., et al., "High-Level Production of Recombinant Human Parathyroid Hormone 1-34", *Applied and Environmental Microbiology*, 64(2), 1998, 526-529.

Wingender, E., et al., "Expression of Human Parathyroid Hormone in *Escherichia coli", The Journal of Biological Chemistry*, 264(8), (1989), 4367-4373.

* cited by examiner

*Primary Examiner* — Michele K Joike

*Assistant Examiner* — Antonio Galisteo Gonzalez

(74) *Attorney, Agent, or Firm* — Schwegman, Lundberg & Woessner, P.A.

(57) ABSTRACT

The present invention discloses a process for the preparation of rhPTH (1-34) also known as teriparatide by construction of a novel nucleotide, as an NcoI.IXhoI fragment as set forth in SEQ. ID. No.:1 encoding a chimeric fusion protein as set forth in SEQ.ID. No.:2 comprising of a fusion partner consisting of 41 amino acids belonging to *Escherichia coli* β-galactosidase (LacZ) gene, an endopeptidase cleavage site, rhPTH (1-34) gene fragment, cloning the said nucleotide in an expression vector under the control of T7 promoter, transforming *Escherichia coli* with the said vector and expressing the chimeric fusion protein in fed batch fermentation. The present invention further discloses a low feed rate lactose induction for optimized expression of rhPTH (1-34) in *Escherichia coli*. The present invention also discloses an unique, novel two step orthogonal purification process for rhPTH (1-34) comprising of cation exchange chromatography optionally followed by preparative chromatography selected from HIC or RP-HPLC to yield a target protein of ≧99% purity. The present invention discloses a simple, cost-effective, environmentally benign method of producing high purity rhPTH (1-34).

5 Claims, 16 Drawing Sheets

ORTHOGONAL PROCESS FOR PURIFICATION OF RECOMBINANT HUMAN PARATHYROID HORMONE (RHPTH) (1-34)

PRIORITY

This application is a nationalization under 35 U.S.C. 371 of PCT/1N2007/000573, filed Dec. 6, 2007 and published as WO 2009/019715 A1, on Feb. 12, 2009, which claimed priority under 35 U.S.C. 119 to Indian Application No. 1543/MUM/2007 filed on Aug. 9, 2007; which applications and publication are incorporated herein by reference and made a part hereof.

FIELD OF INVENTION

The present invention relates to a process for the preparation of rhPTH (1-34) also known as teriparatide by construction of a novel nucleotide, as an NcoI/XhoI frament as set forth in Seq. ID No. 1 encoding chimeric fusion protein as set forth in Seq. ID No.2 comprising of a fusion partner consisting of 41 amino acids belonging to *Escherichia coli* β-galactosidase gene, an endopeptidase cleavage site, hPTH (1-34) gene fragment, cloning the said nucleotide in an expression vector under the control of T7 promoter, transforming *Escherichia coli* with the said vector and expressing the chimeric fusion protein in fed batch fermentation. The present invention further relates to low feed rate lactose induction for optimized expression of rhPTH (1-34) *Escherichia coli*. The present invention still further relates to an unique, novel two step orthogonal purification process for rhPTH (1-34) comprising of cation exchange chromatography optionally followed by preparative chromatography selected from HIC or RP-HPLC to yield a target protein of ≧99%. The present invention relates to a simple, cost-effective, environmentally benign process of producing high purity rhPTH (1-34).

BACKGROUND OF THE INVENTION

Parathyroid hormone is an 84 amino acid peptide secreted by the parathyroid gland. It's physiological role is maintaining serum calcium, and bone remodelling (Dempstor D. W. et al., Endocrine Reviews, 1993, 14, 690-709). The remodelling of bone is typically a 3 to 6 months process wherein there is a coupling between bone resorption and bone formation. Estrogens, vitamin D, bisphosphonates are known to inhibit bone resorption where as rhPTH (1-34), an anabolic agent, increases bone mass. Osteoporosis is a disease that makes a bone susceptible to fracture and rhPTH (1-34) is a peptide drug that has revolutionized treatment of osteoporosis. RhPTH (1-34) when given alone stimulates bone mass formation and causes a net increase in bone mass in each remodeling cycle, wherein bone mineral density is increased by 10% per year typically in lumbar spine area.

Parathyroid hormone (PTH) is secreted by the parathyroid glands in response to a decrease in plasma calcium concentrations and has several effects that act to restore normal calcium levels. It has been shown that PTH has both anabolic and catabolic effects on the skeleton. Persistent elevation of PTH causes increased bone resorption, whereas intermittently administered PTH results in enhanced bone formation (Canalis, E., Hock, J. M., and Raisz, L. G. (1994) in The Parathyroidds: Basic and Clinical Concepts, ed by Bilezikian, J. P., Marcus, R., and Levine, M., Raven Press Ltd., NY) although the cellular mechanism of this dual effects is not clear yet.

PTH is biosynthesized as a 115-amino acid precursor, preproparathyroid hormone (preproPTH). Although the anabolic actions of PTH(1-84) have been known, the actual structural requirement for full biological activity lies in the residues 1 through 34 in the N-terminal of the molecule (PNAS 68, 63-67, 1971; Endocrinology 93, 1349-1353, 1973).

PTH is particularly sensitive to oxidation especially at its methionine residues, Met8 and Met18 and it requires the intact N-terminal sequence for preserving its bioactivity. Frelinger, A. L., et al, (J. Biol. Chem., (1984) 259 (9), 5507-5513) developed a method to separate the methionine oxidized PTH from the native molecule and have shown that the potency of the oxidized molecule is dramatically less than the native PTH. For its comparable bioactivity to the full length PTH, PTH (1-34) requires both the N & C-terminal helical conformation as shown by Jin. L. et al, (J Biol. Chem., (2000) 275 (35), 27238-44. Their model proposes a receptor binding pocket for the N-terminus of PTH(1-34) and a hydrophobic interface with the receptor for the C-terminus of PTH(1-34). Pellegrini M, et al., J. Biol. Chem. (1998) 273 (17), 10420-427 elucidates the high resolution structures of hPTH(1-34) in aqueous solution investigating the effect of pH and salt concentration on secondary and tertiary structures by CD and NMR. The helix content of PTH(1-34), based on CD spectra, increases in the presence of acidic buffer as against benign water. The NMR studies confirm the presence of helical structure localised to the N- & C-terminal part of hPTH(1-34). The molecule outside the context of receptor interaction is far too flexible to prefer any definite secondary or tertiary fold, wherein experimental distance restraint at 0.06 A° gives a flexible rod shape without receptor interaction and "U" shape to the protein while interacting with the receptor. It has been shown that intermittent exposure of the ligand to its receptor has a preferred anabolic effect.

Cloning and expression of a therapeutic protein poses an early challenge in having an appropriate genetic material. Oligonucleotide primers used for cloning should not be degenerate, should have comparative tm and most land at an unique location in the gene of interest. RNA transcript of PTH (1-84) gene is found to be positive in liver, kidney, brain, and placental human tissues. Gene specific primers when used with polymerase chain reaction are suitable in an RT-PCR reaction to clone in the cDNA fragment of specific sequence. It is advisable to fully sequence the insert prior to recloning of the gene. It is well known in the art about many *Escherichia coli* expression vectors available for suitably ligating a cloned fragment, e.g. HB101, JM109, BL21(DE3), TOP10 for high level heterologous expression of recombinant proteins. Primer pairs used to clone in the tag nucleotide sequence can be engineered to contain restriction sites for sequential cloning steps which contain gene of interest with protease cut site and affinity tag.

U.S. Pat. No. 5,496,801 teaches the hPTH preparations that exhibit storage stability in terms of the hormone composition and stability. U.S. Pat. No. 5,496,801 advocates the lyophilization of hPTH (1-84) with mannitol as a cryoprotectant and a non-volatile citrate buffer in the pH range of 3.5 to 6.5 to yield a stabilized ready to use liquid formulation for parenteral administration.

U.S. Pat. No. 4,086,196 discloses for the first time that all fragments of PTH greater than 1-27 hPTH and ($Ala^1$)-hPTH (1-27) have useful biological properties. U.S. Pat. No. 4,086,196 inherently claims hPTH (1-X) and $Ala^1$hPTH (1-X) wherein X is Ser or Ala.

U.S. Pat. No. 4,086,196 also teaches the synthesis of hPTH (1-34) by Solid Phase Peptide Synthesis (SPPS) by the methods well known in the art. U.S. Pat. No. 4,086,196 also discloses the recovery of the bioactive hPTH (1-34) by gel filtration followed by ion exchange chromatography on Whatman-CM-52 and elution carried out following linear gradient using ammonium ions as counter ions. The chief limitations of gel filtration chromatography (GFC) are slow separation and lower peak resolution attributed to factors inclusive of improper matrix selection, column length, high flow rate and large dead spaces entrapped within the column. However, GFC is indeed an attractive option for desalting and buffer exchange for peptide and protein purification. Also chemical synthesis often involves high risk and cost, and although production via recombinant genetic technology has been expected to replace this process, the yield has so far been insufficient. Moreover, the synthesis thereof requires utilizing techniques which require a high level of skill and expertise. Accordingly, the production of hPTH using recombinant DNA techniques is desirable Because of its ease of cultivation, low cost and high production potential, *Escherichia coli* is a preferred host to express and purify pharmaceutically important proteins. However in the case of hPTH due to inherent instability associated with direct expression of the protein (Morelle et al 1988, Biochim. Biophys. Acta 950, 459-462.) a fusion protein strategy has been adopted. Fusion partners commonly used include β-galactosidase, cro-β-galactosidase, hGH, Trx and phospho ribulokinase (Suzuki, Y et al, Appl. Env. Micro 1998, 64, 526-529, Wingender E et al, J. Biol. Chem 264, 4367-4373, Gardella T J et al, J. Biol. Chem 26, 15854-15859, Xiang Yang Fu et al, Biotechnol. Prog 2005, 21, 1429-1435, WO/1999/005277, C12N15/62) for expression and downstream purification of this protein. Also the number of amino acids that were used from β-galactosidase as fusion partner were different for different proteins. In case of insulin and proinsulin (Shen, S-H. (1984), Proc. Natl. Acad. Sci. USA 81: 4627-4631, Guo, L. (1984), Gene 29: 251-25) the β-Gal fusion partner was much longer than PTH on the same promoter back (T7 and lac promoter, Massayuki, Y et al. (1997), U.S. Pat. No. 5,670,340). Much literature reports the expression of fusion protein as insoluble aggregates by subjecting to a series of denaturation and refolding steps. In cases where β-galactosidase have been used as the fusion partner for PTH (1-34), final yields ranging from 20 mg/L to 500 mg/L have been reported using Isopropyl beta galactoside (IPTG) as the inducer at 1 mM concentration. However, the use of IPTG for the large-scale production of recombinant proteins is undesirable because of its high cost and toxicity (Donovan et al., 1996; Figge et al., 1988; Gombert and Kilikian, 1998; Ksinski et al., 1992). Oldenburg K. R., et al (Protein Exp. Purification 5(3), 278-284, (1994)) describes a method for high-level expression of rPTH(1-34) in *E. coli*, with polyhistidine leader peptide and eight copies of PTH gene. Oldenburg K. R., et al also teaches the fusion protein capture by Ni chelation chromatography followed by a cyanogen bromide (CNBr) cleavage and a purification by RP-HPLC with a final yield of 300 mg/L of highly purified biologically active hPTH(1-34). Use of cyanogen bromide poses an environmental threat in terms of safe handling Wand disposal which severely restricts the use.

EP 794255 disclose purification of rhPTH (1-34) using Kex2 cutting from its chimera. Suzuki Y, et al., (Applied and Environmental Microbiology 64(2), 526-529 (1998)) obtained 0.5 g of >99% pure hPTH (1-34) from one liter of *Escherichia coli* culture using different lengths of β-galactosidase linker along with His-tag fusion partner. Suzuki Y., et al., disclose the isolation of the inclusion bodies, solublisation in 8M urea, dilution to have a urea concentration of 3M followed by Kex2 digestion followed by intermediate purification by ion exchange chromatography, and final polishing by two steps of reverse phase chromatography. Suzuki Y. et al., teaches that, Kex2 a secretory type Kex2 protease from yeast used for enzymatic cleavage is significantly affected by the 3M Urea concentration required for maintaining the fusion protein in the soluble form, even addition of 2.5 mM $CaCl_2$ to suppress the inactivation lead to precipitation of the fusion protein which resulted in use of molar ratio of 1:2000 for enzyme to substrate. Suzuki Y. et al., thus though reports high yield of the target protein but Kex2 usage still accounts for too large a proportion of the primary cost of the production process. Suzuki Y. et al., also explicitly teaches the use of 97,117 and 139 amino acid fragments of β-galactosidase as fusion partner spaced by linker having SVKKR (SEQ ID NO:9) as the cleavage site for Kex2 accounts for high yield of the fusion protein.

Jin. L., et al, J Biol. Chem. (2000), 275(35), 27238-27244) discloses a purification process for LY 333334 molecule rhPTH(1-34) by solublisation in 7M Urea and capture on a reverse phase column, followed by a FF SP cation exchange column purification using a NaCl gradient subsequently followed by a RP-HPLC method wherein the purified material in 20 mM Glycine buffer pH 9 is freeze dried. This is a prosolvent method and may be hazardous at manufacturing scale. Fu, Xiang-Yang et al, (Biotechnology Progress (2005), 21(5), 1429-1435) teaches a method to purify a thioredoxin fusion of PTH(1-34) from BL21(DE3) cells by use of Triton-X 100 and heat denaturation induced partial purification by precipitation. The heating is done at 80° C. for 15 minutes. The method treats the protein at high temperature which is generally undesirable for proteins and peptides. CN 1417231 describes a process for recovery of recombinant PTH(1-34) by fermentation, followed by inclusion body purification, renaturation, thrombin digestion and purification over cation exchange chromatography. CN 1424325 describes a GST fusion PTH(1-34) peptide (with GSP as the cleavage site) digested with thrombin, purification on chymotrypsin affinity column, digestion with proline endopeptidase and further chromatographic purification. The process is cumbersome and use of two proteases adds to the cost of the purification process limiting the commercial exploitation of the same. Biochem. Biophys. Res. Commun., 166, 50-60 (1990) documents a cDNA approach for the synthesis of hPTH.

Chen, J. Y. et al, ((2004), 40 (1), 58-65) discloses PTH(1-34) purification, by expression of PTH (1-34) as a chimera with cellulose binding domain, cleaving PTH(1-34) by Factor Xa, purifying with cellulose resin and RP-HPLC to yield 3 mg/L which is a very low yielding process with no commercial viability. GST fusion technology for PTH (1-34) production is also well known in the art. Gram Hermann et al, (Bio/Technology (1994), 12(10), 1017-23) describes a method for purification of PTH(1-34) using dipeptidyl peptidase IV. Wingender E., et al, (J Biol. Chem. (1989), 264(8), 4367-4373) expressed PTH in *E. coli* as cro-β-galactosidase-hPTH fusion protein. An yield of about 250 mg of fusion protein was obtained from 1 L of culture which they solublised in Urea and further, an acid treatment was used to release PTH. Acid cleavage conditions are plagued by limitations due to formation of deamidated or oxidised related protein impurities which are difficult to separate in some proteins and moreover acidic pH poses harsh conditions detrimental to protein bioactivity.

EP 0483509B1 relates to a codon optimized synthetic gene producing hPTH corresponding to the amino acid sequence of hPTH, DNA containing it, a host cell transformed by the DNA and a method for producing hPTH using the transformant in *E. coli* with IPTG induction. EP083509B1 discloses the purification of the PTH expressed by RP-HPLC. Use of organic solvents as eluants in RP-HPLC may harm the protein which poses scalability problem. U.S. Pat. No. 5,208,041 teaches production of essentially pure hPTH characterized by single peak migration when analyzed by capillary electrophoresis at 214 um, and by an EC50 as determined in the UMR 106-based adenylate cyclase assay of not more than 2 nM, by purifying the crude hPTH by RP-HPLC with a cationic ion-pairing agent as triethylamine phosphate. U.S. Pat. No. 5,208,041 also discloses subjecting the hPTH obtained either from mammalian tissue, from microbial sources of PTH or from synthetic sources to at least one column fractionation step prior to RP-HPLC. U.S. Pat. No. 5,208,041 exemplifies the purification process by subjecting the whole broth to pH adjustment from 4.0 to 8.0 with glacial acetic acid, clarification by centrifugation, followed by loading on to an ion exchange chromatography column of S-Sepharose, further subjecting the eluate to an intermediate purification step by loading on to HIC column of Phenyl Sepharose and finally purifying by RP-HPLC using C18 column with triethylamine phosphate as the ion pairing agent. U.S. Pat. No. 5,208,041 cites the detection by capillary electrophoresis of 4 previously undetected minor peaks eluting ahead of PTH peak and some trailing peaks which were not detected by using trifluoroacetic acid (TFA) or heptafluorobutyric acid (HFBA) as ion-pairing agent thus leading to the recovery of essentially pure hPTH, U.S. Pat. No. 5,208,041 does not in any way teaches the use of HIC as final purification step to obtain a purified hPTH (1-34) with ≧99% purity which is the focus of the present invention. U.S. Pat. No. 5,457,047 relates to DNA sequences coding for PTH variants, expression vectors, bacterial hosts, uses and therapeutic compositions. U.S. Pat. No. 5,457,047 discloses hPTH purification by means of CM-cellulose in batch mode followed by RP-HPLC from cro-β-galactosidase-hPTH fusion protein.

U.S. Pat. No. 6,590,081 teaches the synthesis of pure crystalline form of teriparatide, and methods of preparation and purification of the fragmented PTH. U.S. Pat. No. 6,590,081 explicitly teaches the advantage of crystalline form of the hormone to be product purity and storage stability. Also to create more potent and orally available analogs of PTH, detailed structural information on the peptide should aid in characterizing the molecule interactions between the ligand and the receptor. U.S. Pat. No. 6,590,081 also discloses that the crystalline PTH may also be formulated into other compositions such as for example, tablets, capsules or suppositories, as the same is easily dissolved in sterile solution in vials. U.S. Pat. No. 6,590,081 claims the cubic, hexagonal and plate like crystals of hPTH(1-34) and process for purifying the PTH to obtain the same.

Liu, Q., et al., in Protein Expr Purif., 2007 August, 54(2): 212-9, disclose a large scale preparation process of hPTH (1-84) from *E. coli* using a soluble fusion protein strategy, by constructing a codon-optimized synthetic gene encoding hPTH(1-84) and cloning the same in pET32a (+) vector, expressing in *E. coli* BL21 (DE3) cells as soluble His(6)-thioredoxin-hPTH(1-84) fusion protein. Liu, Q., et al., follows a sequel of purification steps of capture by immobilized metal affinity chromatography, followed by enterokinase cleavage and terminally subjecting the same to size exclusion chromatography with a quantified yield of 300 mg/L with a purity of 99% after harvesting the soluble fusion protein.

Orthogonal process design is the foundation of well-controlled purification procedures (Gagnon P. The secrets of Orthogonal Process Development. Validated Biosystems, 2006:www.validated.com/revalbio/pdffiles/orthopd.pdf). The idea is that combining the steps with the greatest complementarity should provide the best overall purification. The strongest embodiment of the concept is usually achieved when respective steps are based on distinct separation mechanisms. A two-step process that contains one fractionation step based on product size and another on product charge would be considered orthogonal; similarly, a process with one step based on product charge and another on hydrophobicity would also be orthogonal. An important feature of orthogonal process design is that the purification capability of any one step is measurable only within the context of its potential partner.

The present invention comprises an orthogonal process for purification of rhPTH (1-34) coupling cation exchange chromatography to HIC to achieve a purity of ≧99% with good yield.

The large-scale production of therapeutic proteins faces several challenges, such as short development timelines, cost considerations, and ever increasing quality requirements. State-of-art isolation and purification technologies, specifically orthogonal separation principles, are of enormous importance to speed up development, shorten processing times, and cut the production costs. Preparative chromatography has advanced significantly with regard to matrix stability or availability of selectivities, and provides the premier technology in biomolecule purification to purities above 95%. Hydrophobic interaction chromatography (HIC) has gained popularity in recent years since it offers orthogonal separation power to widely used purification techniques based on ionic interactions. HIC is often an excellent choice subsequent to ion exchange chromatography in a protein purification procedure. Both techniques have an extremely broad applicability and are canonical approaches with respect to one another (i.e. separation according to hydrophobicity and charge respectively). Furthermore, material eluted with a salt gradient in an ion exchange separation requires a minimum of sample treatment. On the other hand, while exerting similar selectivity, HIC is less denaturing compared to reverse phase chromatography, using more hydrophobic ligands and organic solvents. At an industrial scale, explosion-proof production suites are required for the handling of the toxic organic solvents, the disposal of large quantities of which is costly. Hence an orthogonal approach of coupling ion exchange chromatography followed by HIC is a cost-effective, environmentally benign platform technology for large scale production of recombinant fusion proteins.

Above cited prior art neither explicitly teach the orthogonal approach of purification of hPTH(1-34) by coupling cation exchange chromatography as an intermediate purification step to HIC as the final purification strategy, nor, reports the use of novel lactose induction with good yield of hPTH (1-34), which is the prime focus of the present invention.

The present invention has an unique, novel feature of use of an orthogonal approach of two step purification process of cation exchange chromatography optionally followed by preparative chromatography selected from HIC or RP-HPLC. The present invention discloses a simple, cost-effective, environmentally benign method of producing high purity hPTH (1-34). Other unique feature of the present invention is lactose induction for a fed batch production strategy for optimized expression of hPTH (1-34) in prokaryotic host. Another feature of the present invention is construction of a chimeric fusion protein comprising of a fusion partner consisting of 41 amino acids of *Escherichia coli* β-galactosidase (LacZ) gene, an endopeptidase cleavage site, rhPTH gene fragment wherein the fusion partner, the β-galactosidase gene is chosen being a protein native to *Escherichia coli*, high % GC content, corresponding peptide secondary structure, the secondary structure of ribonucleotide translating the same, and the pI of the fusion fragment as an aid facilitating downstream processing.

OBJECTS OF THE INVENTION

A first aspect of the present invention is a process for synthesis of rhPTH (1-34), said process comprising:

i. isolating the total RNA from tissue source, ii. constructing a cDNA coding chimeric nucleotide ORF as a NcoI/XhoI fragment as set forth in SEQ. ID NO.:1 by amplification of the cDNA by RT-PCR using gene specific primers selected from SEQ. ID NO.:3, SEQ. ID NO.:4, SEQ. ID NO.:5, SEQ. ID NO.:6, SEQ. ID NO.:7 and SEQ. ID NO.:8 encoding rhPTH (1-34) chimeric fusion protein as set forth in SEQ. ID NO.:2, iii. transforming *Escherichia coli* with an expression vector containing chimeric nucleotide ORF as a NcoI/XhoI fragment as set forth in SEQ. ID NO.:1 encoding rhPTH (1-34) chimeric fusion protein as set forth in SEQ. ID NO.:2 wherein the chimeric fusion protein consists of an affinity handle, a fusion partner, an endonuclease cleavage site and rhPTH (1-34) peptide, iv. culturing the transformed *Echerichia coli* of step iii. for expression of chimeric fusion protein in the presence of an inducer, v. isolating the chimeric fusion protein from the culture in the form of inclusion bodies, vi. capturing the rhPTH (1-34) chimeric fusion protein of step v, vii. digesting the rhPTH (1-34) chimeric fusion protein of step vi., viii. purifying the rhPTH (1-34) obtained by step vii by an orthogonal process.

A second aspect of the present invention discloses the use of low feed rate lactose induction for the expression of chimeric fusion protein rhPTH (1-34) wherein the lactose induction is in the range of about 10% to 30% of the total protein.

A third aspect of the present invention is an orthogonal process for purification of rhPTH (1-34), said process comprising:

i. capturing the solubilized chimeric fusion protein as set forth in SEQ. ID NO.:2 using expanded bed chromatography, ii. digesting the eluted chimeric fusion protein of step i by endopeptidase to yield target protein, iii. purifying the target protein by cation exchange chromatography to a purity of ≧98%, iv. optionally polishing the target protein by HIC or RP-HPLC to a purity of ≧99%.

A fourth aspect of the present invention discloses an orthogonal process for purification of rhPTH (1-34) wherein the solubilized chimeric fusion protein is captured on streamline chelating sepharose column under denaturing condition, captured chimeric fusion protein is digested by enterokinase in urea concentration in a range from 500 mM to 4000 mM for a period from 4 to 6 hours, the digested target protein is purified to a purity of ≧98% on SP-XL cation exchange column and the eluted target protein is optionally polished by HIC on phenyl sepharose to a purity of ≧99%.

A fifth aspect of the present invention is rhPTH (1-34) in liquid form wherein the rhPTH (1-34) is neither in crystalline form nor in amorphous form.

Other aspects and advantages of the present invention will be apparent upon consideration of the following detailed description which includes numerous illustrative examples of the practice of the invention.

BRIEF DESCRIPTION OF THE ACCOMPANYING DRAWINGS

The manner in which objects and advantages of the invention may be obtained will appear more fully from the detailed description and accompanying drawings, which are as follows:

FIG. 1 shows PCR amplified product on 1% agarose gel, where 281 bp fragment covering the lacZ portion of the ORF and 141 bp region which contains the corresponding nucleotides of 1-34 amino acids is shown in Lane 1. These fragment were further digested to 281 bp with NcoI/SalI (Lane 2) and 141 bp with SalI/XhoI (Lane 3). Lane 4: pET19b vector after digestion with NcoI/XhoI and gel purification for the use of cloning, Lane 5: 100 bp DNA marker (promega).

FIG. 2 shows Miniprep DNA digested with NcoI/XhoI showing presence of positive clones with the insert of our interest β-galactosidase-hPTH (1-34) (LacZ) fragment. Lane 2-12 and 14: showing 342 bp of Fragment 4) of β-galactosidase-hPTH (1-34) insert band (shown by an arrow). 5643 bp of pET19b vector fragment is shown at the top (shown by an arrow head). Lane 13: confirming the size of the NcoI/XhoI digested vector fragment which shows absence of the 342 bp of insert band.

FIG. 3 shows the map of pET-β-galactosidase-hPTH (1-34) insert in pET-19b vector.

FIG. 4 shows the RE analysis with NcoI/XhoI on the positive clones BL21(DE3) transformants, showing the presence of digested fragment, 342 bp (shown by arrow). Lane 1: Gene ruller ladder mix, Lane 2-13: Clone #48 and 49. Same was done with the other positive clones, mentioned in FIG. 3.

FIG. 5 shows the RE analysis with NcoI/XhoI on the positive clones BL21(DE3) transformants, showing the presence of digested fragment, 342 bp (shown by arrow). Lane I: Gene ruller ladder mix, Lane 2-6: Clone#48 and 49. Same was done with the other positive clones, mentioned in FIG. 4.

DETAILED DESCRIPTION OF INVENTION

Figure 1:
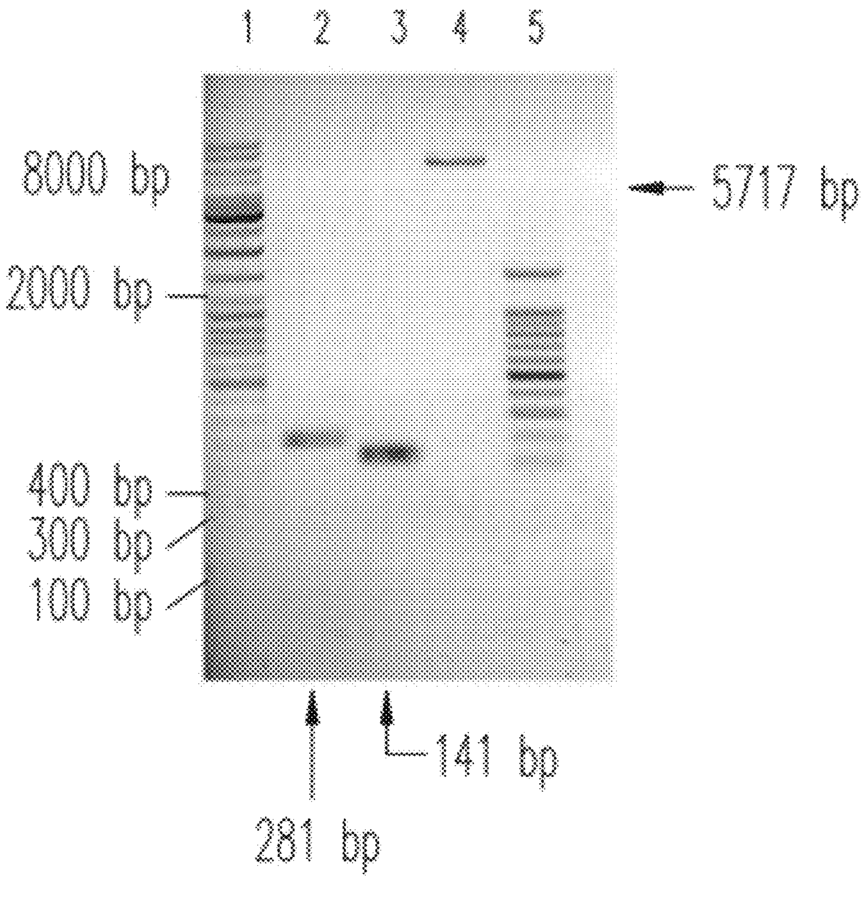

One embodiment of the present invention is directed to a process for synthesis of rhPTH (1-34), said process comprising:

i. isolating the total RNA from tissue source, ii. constructing a cDNA coding chimeric nucleotide ORF as a NcoI/XhoI fragment as set forth in SEQ. ID NO.:1 by amplification of the cDNA by RT-PCR using gene specific primers selected from SEQ. ID NO.:3, SEQ. ID NO.:4, SEQ. ID NO.:5, SEQ. ID NO.:6, SEQ. ID NO.:7 and SEQ. ID NO.:8 encoding rhPTH (1-34) chimeric fusion protein as set forth in SEQ. ID NO.:2, iii. transforming *Echerichia coli* with an expression vector containing chimeric nucleotide ORF as a NcoI/XhoI fragment as set forth in SEQ. ID NO.:1 encoding rhPTH (1-34) chimeric fusion protein as set forth in SEQ. ID NO.:2 wherein the chimeric fusion protein consists of an affinity handle, a fusion partner, an endonuclease cleavage site and rhPTH (1-34) peptide, iv. culturing the transformed *Echerichia coli* of step iii. for expression of chimeric fusion protein in the presence of an inducer, v. isolating the chimeric fusion protein from the culture in the form of inclusion bodies, vi. capturing the rhPTH (1-34) chimeric fusion protein of step v, vii. digesting the rhPTH (1-34) chimeric fusion protein of step vi., viii. purifying the rhPTH (1-34) obtained by step vii by an orthogonal process.

Other embodiment of the present invention is directed to the use of low feed rate lactose induction for the expression of chimeric fusion protein rhPTH (1-34) wherein the lactose induction is in the range of about 10% to 30% of the total protein.

Another embodiment of the present invention is directed to an orthogonal process for purification of rhPTH (1-34), said process comprising:

i. capturing the solubilized chimeric fusion protein as set forth in SEQ. ID NO.:2 using expanded bed chromatography, ii. digesting the eluted chimeric fusion protein of step i by endopeptidase to yield target protein, iii. purifying the target protein by cation exchange chromatography to a purity of ≧98%, iv. optionally polishing the target protein by HIC or RP-HPLC to a purity of ≧99%.

Still another embodiment of the present invention is directed to an orthogonal process for purification of rhPTH (1-34) wherein the solubilized chimeric fusion protein is captured on streamline chelating sepharose column under denaturing condition, captured chimeric fusion protein is digested by enterokinase in urea concentration in a range from 500 mM to 4000 mM for a period from 4 to 6 hours, the digested target protein is purified to a purity of ≧98% on SP-XL cation exchange column and the eluted target protein is optionally polished by HIC on phenyl sepharose to a purity of ≧99%.

Still another embodiment of the present invention is directed to rhPTH (1-34) in liquid form wherein the rhPTH (1-34) is neither in crystalline form nor in amorphous form.

The term "cDNA" or complementary DNA as used herein refers to synthetic DNA reverse transcribed from a specific RNA through the action of the enzyme reverse transcriptase.

The term "ORF" or Open Reading Frame as used herein refers to a portion of oraganism's genome which contains a sequence of bases potentially encoding a protein.

The term "β-galactosidase" and "LacZ" are used herein as synonymous terms.

By "gene specific primers" is meant primers sufficiently complimentary to hybridize with a target polynucleotide for the synthesis of the extension product of the primer which is complimentary to the target polynucleotide.

HIC imparts minimum structural damage to the biomolecules is minimum and its biological activity is maintained, due to a weaker interaction than affinity, ion exchange or reversed-phase chromatography (RPC) (Fausnaugh et al., 1984; Regnier, 1987). HIC is an alternative way of exploiting the hydrophobic properties of proteins, working in a more polar and less denaturing environment than RPC, since this technique requires the use of non-polar solvents for the protein elution due to strong binding to adsorbent (El Rassi, 1996).

PTH is a single chain 84-amino acid peptide in which the structural requirements for full biologic activity are satisfied by the first 34 $NH_2$-terminal amino acids. Deletion of a few amino acids from either the $NH_2$ or COOH terminus of the active fragment PTH (1-34) results in a progressive decline in biologic activity, such that the continuous sequence region 2-26 has been designated the minimum sequence necessary for biologic activity as determined by activation of renal adenylate cyclase. Rossenblatt, M. et al., explicitly teaches that the synthetic analogue (Nle-8, Nle-18, Tyr-34)bPTH-(3-34) amide, which incorporates modifications shown with bPTH (1-34) to both enhance biologic activity and confer resistance to oxidation, will inhibit bPTH (1-84) activity when present with the native hormone in equimolar amounts. The known biological actions of PTH are expressed in a fragment that contains only the first 34 amino acids (Tregear, G. W., Rietschoten, J. V., Greene. E., Keutmann, H. T., Niall, H. D., Reit, B., Parsons, J. A., and Potts, J. T., Jr. (1973) Endocrinology 93, 1349-1353)), and the function of the carboxyl-terminal 50 residues is not known. The interaction of 1-34 PTH with its receptors is altered both by oxidation of the methionine residue at positions 8 and 18 (Tashjian, A. H., Ontjec, D. A., and Munson, P. L. (1964) Biochemistry 3, 1175-1182; Frelinger, A. L., III, and Zull, J. E. (1984) J. Biol. Chem. 259, 5507-5513; Frelinger, A. L., III, and Zull, J. E. (1986) Arch. Biochem. Biophys. 244, 641-649) and by deletion of amino acids at the amino terminal end of the hormone (Martin, K. J., Bellorin-Font, E., Freitag, J., Rosenblatt, M., and Slatopolsky, E. (1981) Endocrinology 109, 956-959; Mckee, R. L., Goldman, M. E., Caulfield, M. P., deHaven, P. A., Lave, J. J., Nutt, R. F., and Rosenblatt, M. (1988) Endocrinology 122, 3008-3010; Goldman, M. E., McKee, R. L., Caulfield, M. P., Reagen, J. E., Levy, J. J., Gay, C. T., DeHaven, P. A., Rosenblatt, M., and Chorev, M. (1988) Endocrinology 123, 2597-2599). The oxidized peptides are full agonists with reduced affinity (Frelinger, A. L., III, and Zull, J. E. (1984) J. Biol. Chem. 259, 5507-5513; Frelinger, A. L., III, and Zull, J. E. (1986) Arch. Biochem. Biophys. 244, 641-649), but the amino-terminal deleted peptides are partial agonist or antagonists with reduced affinity (Martin, K. J., Bellorin-Font, E., Freitag, J., Rosenblatt, M., and Slatopolsky, E. (1981) Endocrinology 109, 956-959; Mckee, R. L., Goldman, M. E., Caulfield, M. P., deHaven, P. A., Lave, J. J., Nutt, R. F., and Rosenblatt, M. (1988) Endocrinology 122, 3008-3010). Oxidation of residue 8 has the greatest impact on hormone affinity, and deletion of residues 1 and 2 produces the most dramatic effects on biological activity. Thus, 3-34 PTH is a very weak agonist, and the 7-34 fragment is an antagonist. It appears that either the altered residues are directly involved in receptor binding or that oxidation or deletion induces secondary or tertiary structural changes in the peptide so that receptor binding and/or activation is defective. Hence, an unique sensitive orthogonal process for synthesis of N and C terminal intact full length rhPTH (1-34) which exhibits bioactivity is an essential feature of the invention wherein the rhPTH (1-34) separation from other impurities is achieved yielding a purity of ≧99% with good process yield. Oxidized impurities are often generated during aqueous purification on the rhPTH (1-34) by exposure of the peptide to air. Hence the literature reports the use of RP-HPLC as the final polishing step wherein the organic solvents used for elution prevent aerial oxidation. In lieu of the advantages offered by HIC, in terms of cost saving by avoiding usage of HPLC-grade organic solvents and the additional cost incurred in removing traces of organic solvents to desirable limits, and disposal and mainly handling of volatile solvents on large scale, motivated the inventors to develop a simple, environmentally benign, cost-effective optimized orthogonal process of coupling cation exchange chromatography to HIC to achieve a purity of ≧99% for rhPTH (1-34). The present invention thus avoids generation of any oxidized impurities and other related impurities as deamidated peptides by using an aqueous environment for elution and yielding an N and C terminal intact rhPTH (1-34). In the present invention, the intermediate purification step of cation exchange chromatography employing SP-XL column yielded rhPTH (1-34) with a purity ≧98% with an enhanced yield in the range of 300-400 mg/L. The focus of the present invention is thus synthesis of highly purified stable rhPTH (1-34) in liquid form.

A wide variety of commercially important proteins have been produced in *Escherichia coli*. Thus considerable efforts were made to optimize the volumetric yield of recombinant proteins in order to decrease production costs (Lee, 1996). An important characteristic of the promoters used in these systems is their inducibility in a simple and cost effective manner. Use of lactose as an inducer for optimized fed batch expression of the fusion protein is also an essential feature of the present invention.

In the present invention we describe a method to clone PTH(1-34), by amplifying cDNA encoding human PTH 1-84 amino acids using RT-PCR. The cDNA was cloned into a pUC-18 based cloning vector which was used as the template for cloning of the region encoding 1-34 amino acids of hPTH. The target construct was designed in a manner where a novel 41 amino acids of β-galactosidase (LacZ) ($124^{th}$ amino acid to $164^{th}$ amino acid) was taken as a fusion peptide to increase the level of PTH expression at 1 L shake flask as well as in the scaled up fermentation. The peptide adds an advantage of pI for intact recombinant protein and was chosen on the basis of peptide secondary structure and ribonucleotide free energy. A protease cut size e.g., enterokinase was incorporated at the end of lacZ fusion for efficient removal of the fusion partner from the protein of interest. Full ORF is under T7 promoter control inducible with ampicillin as a selection marker.

The cell pellet obtained from fermentation broth was suspended in a buffer, pressure disrupted to lyse the cell by subjecting the cell suspension to repeated cycles of high pressure homogenisation. To this lysed cell suspension, urea crystals are added to a final concentration of 4-8M and stirred for 8-12 hrs to solublise cellular proteins. The solution was then centrifuged or microfiltered to remove the cell debris.

The fusion protein of interest was then purified from the soluble total protein by streamline chelating sepharose. The elution from streamline chelating column containing the fusion protein was then either desalted using G-25 or directly diluted to bring down the final salt concentration. To this solution recombinant Enterokinase was added at a concentration of 1-10 units to 20-100 μg of protein and kept for an 4-12 hrs with urea concentration at 1M. Simultaneously desalting and preparation for enzymatic step was performed.

The solution pH of this digested sample was adjusted to pH 5-7 and bound on an ion exchanger preferably a cation exchanger. The cation exchanger could be either a polymeric bead or sepharose based bead containing sulfopropyl, methylsulfonate or carboxymethyl group attached to them. After loading the sample, the column was washed with low concentration of acetate buffer of about 20-50 mM concentration and bound protein eluted with a gradient of buffer B containing 0.5-1M NaCl. The absorbance at either 254 nm or 280 nm was monitored to check the elution profile. The main peak contains PTH(1-34) which was taken for further purification.

Final purification was done using either HIC or RPC. For HIC, ammonium sulfate or NaCl was added to IEX elution to a final concentration of 1-2M and then the sample was loaded on a HIC column. HIC column could be phenyl, butyl, isopropyl or ether group attached to either polymeric bead or sepharose/agarose based bead. In the present invention both source phenyl and phenyl sepharose have been used. A gradient elution of the bound protein from high salt to low salt in either water or acetate/citrate buffer of 20-50 mM gives rise to >99% pure PTH(1-34). Alternative non-aqueous mode could be RPC step with both C4 silica as well as polymeric reverse phase columns. In the mobile phase A, water containing 0.01%-0.1% TFA or sodium acetate buffer pH 4.0 can be used and mobile phase B could be either acetonitrile or acetonitrile, methanol mixture. A gradient elution with mobile phase B would robustly separate the related impurities and give rise to >99% pure PTH(1-34) fractions. It should be understood that the following examples described herein are for illustrative purposes only and that various modifications or changes in light will be suggested to persons skilled in the art and are to be included with in the spirit and purview of this application and the scope of the appended claims.

EXAMPLES

Example 1

Total RNA Isolation and Synthesis of the $1^{st}$ Strand cDNA

Total RNA was isolated from by "RNAgents For Total RNA Isolation Systems" (Promega, Cat #Z5110). About 2 g of tissue was processed. A strategy was taken where full length PTH cDNA were isolated from several tissue sources e.g., liver, kidney, brain and placenta total RNA. Total RNA pellet was resuspended in 1 ml nuclease-free water and stored at −70° C. Total RNA concentration was about 4 ng/ml. Polyadenylated RNA was pooled with the help of Oligo (dT) 8+12 beads from total RNA as described above. 10 ng of total RNA was used for each reaction. Polyadenylated RNA was reverse-transcribed into single-stranded complementary DNA ($1^{st}$-strand cDNA template) using AMV reverse transcriptase at 42° C. for 1 hr. About 20 ng/ul of $1^{st}$-strand cDNA was obtained. 1st-strand quality was checked by amplifying beta-actin primer pairs.

Example 2

PCR Amplification of Putative 1-84 Amino Acid Containing PTH cDNA from Tissue Sources Based on the full length 1-84 amino acids gene specific primer pair were synthesized for $1^{st}$ strand generation by RT-PCR method. All the above mentioned tissue sources were used for amplification and were found to be positive for PTH. Finally liver was selected for cloning of 1-34 aminoacids domain of PTH into a T7 *E. coli* expression vector system. 476 bp cDNA encoding 1-84 aminoacids was cloned and was the template for further amplification of 1-34 amino acid domain. RT-PCR was done on the mRNA pool using gene-specific primer pair (SEQ ID. NO. 3 & 4) that was developed on PTH cDNA sequence. These pair was used to amplify 476 bp PTH full length cDNA sequence (Fragment 1).

Example 3

Ligation and Transformation

The ligation mixture containing 20 ng-50 ng DNA of Fragment 1 (476 bp) was separately ligated with the pUC-18 based TA-cloning vector and pET-19b vector into JM109 and BL21 (DE3), respectively. To increase the number of transformants plates were incubated overnight at 4° C. Restriction enzyme analysis and Sequence analysis on the positive clones was done to confirm the same. Several positive clones for PTH (1-84) were obtained.

Example 4

Cloning of Human PTH 1-34 Amino Acids by PCR Amplification

In the next step, PCR amplification was done as mentioned down to amplify 1-34 PTH domain using the PTH 1-84 aminoacids containing DNA construct mentioned above. The target construct was designed in a manner where a portion of β-galactosidase (LacZ) was taken as a fusion peptide. A protease cut site e.g., enterokinase was inserted by PCR methods at the end of lacZ for enzymatic removal of it from the mature 1-34 AA, the protein of interest.

The sequence as mentioned below: VDNCDESWLQEGQTRIIFGDVNSAFHL-WGRWVGYGQDSRLP (SEQ ID NO:10) is the β-galactosidase amino acid sequence chimeric to rhPTH (1-34) with EK out site DDDK (SEQ ID NO:11).

A primer pair was then (SEQ. ID NO. 5 & 6) used to amplify the 5'-end of the fusion chimera, lacZ with the His-tag and EK cut site at the 3'-end. This PCR amplified product, 241 bp (Fragment 2) has two RE sites, NcoI and SalI, which was useful during cloning with 1-34 aminoacids together into pET-19b vector. 3'-end of the rhPTH(1-34) was amplified using other set of primer pair (SEQ ID NO. 7 & 8) which was used on the full length PTH (1-84) cDNA to amplify a 141 bp fragment with SalI and XhoI RE sites for cloning immediately after EK cut site.

Example 5

Making of the Final Construct of pET-lacZ-rhPTH(1-34)

Figure 3:
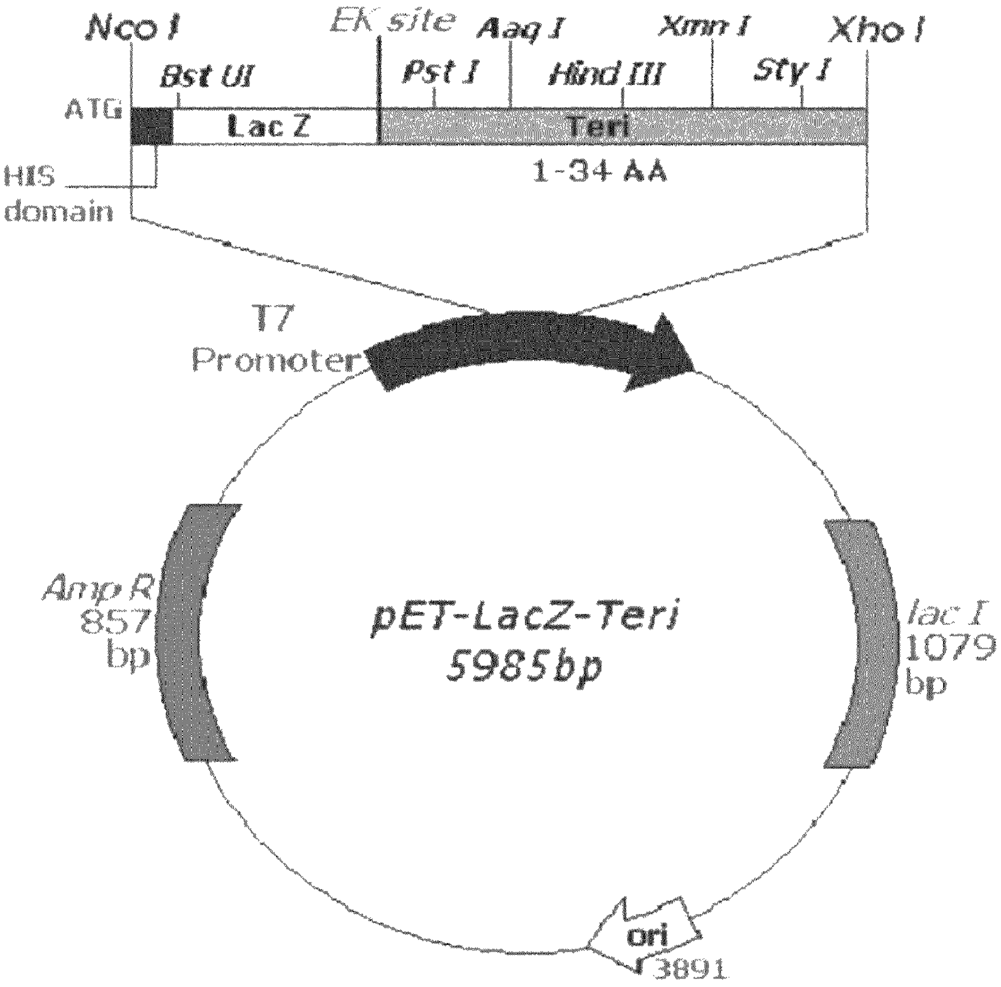

The final construct as shown in FIG. 3, contains the 5-upstream start site with NcoI site along with lacZ sequence, EK cleavage site and the immediate start site of the rhPTH (1-34) sequence drawn after EK cut site and before TCT GTG . . . TAATAA with two stop codons XhoI site CTC GAG. These clone cultures were then grown overnight at 37° C. and stored at −70° C. Full ORF that is translated till the stop codons at the 3'-end immediately after 108 bp (encodes 34 amino acid of rhPTH(1-34)). The mature cDNA is encoding for 34 amino acid including two stop codons is mentioned (FIG. 1*b*).

This ORF was then cloned into pET-19b *E. coli* expression vector at NcoI/XhoI site. Sequential steps have shown below. For final cloning (FIG. 2) and PCR amplification of rhPTH (1-34) a fusion tag (lacZ) was attached at the 5'-end. The full chimera in the cloning vector contains 6× His-lacZ-EK-(1-34) without any signal peptide.

Purification of the Target Fragment 2 and 3:

Gel purified PTH cDNAs were ligated with the pET-19b vector at the NcoI/XhoI RE sites. In lane 2, PCR product 281 bp (Fragment 2, FIG. 1) is showing 5'-end of the lacZ portion with NcoI and SalI site which resides the portion of 6× His-lacZ-EK site. In lane 3, PCR product is showing the start of the putative PTH mature ORF after the signal peptide 1-34 aminoacids (rhPTH(1-34)) with two stop codons. This 141 bp (Fragment 3, FIG. 1) contains SalI and XhoI sites for ligation with the upstream lacZ and EK site. Ligation of the digested Fragment 2 and 3 at the SalI site gives rise to lacZ-rhPTH(1-34) insert fragment of 342 bp (Fragment 4, FIG. 1) which has been ligated with the vector at the NcoI site at 5'-end and XhoI site at 3'-end. Ligation to give the final construct (FIG. 3) and transformation procedures were followed as per Example 3 and screened for the positive transformants by digesting mini-prep extracted DNA with NcoI/XhoI to attain ligated fragment.

Example 6

Confirmation of the Restriction Map

RE analysis was done by using NcoI/XhoI and BglII/XhoI double digestion was done to confirm these positive clones further after transformation of BL21(DE3) with the previously identified positive clones using 50-100 ng of DNA. RE analysis was also done using SalI which has two sites in the pET-lacZ-rhPTH(1-34) construct. 141 bp (Fragment 3) was visible with the enzyme analysis (data not shown).

Several positive clones we have achieved in BL21(DE3) strain background which were analyzed by using double digestion with NcoI/XhoI enzyme combination.

Figure 4:
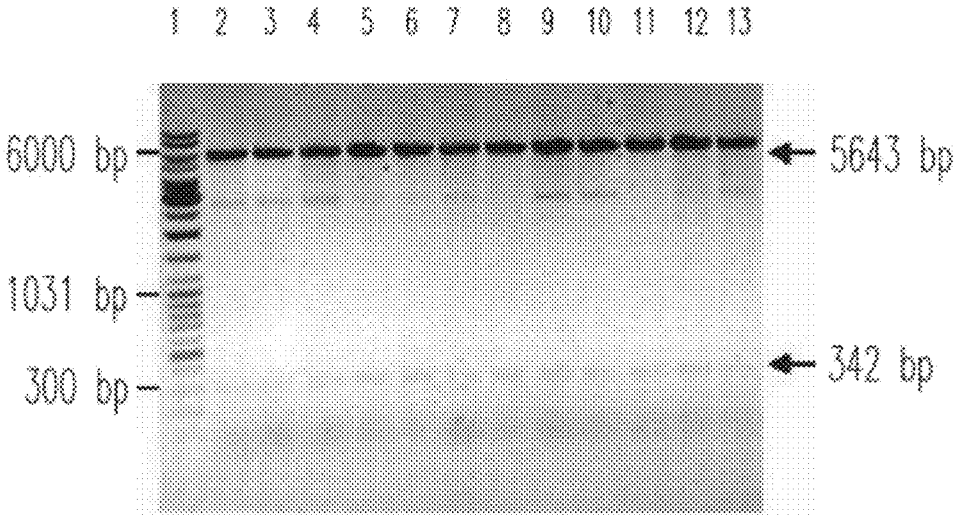
Figure 5:
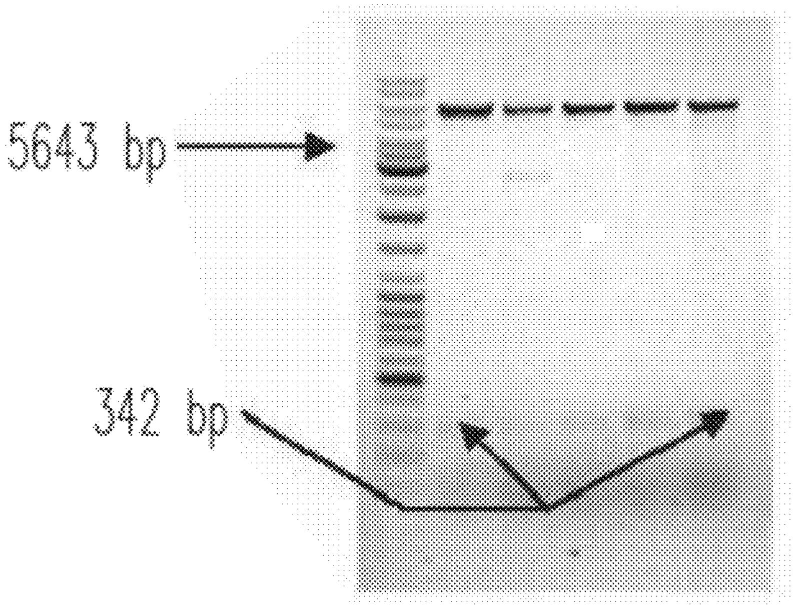

Results showed the right size, 342 bp of the insert fragment (Fragment 4). By using BglII/XhoI and several other combinations of restriction enzymes e.g., BamHI/SalI, SalI these clones were then checked before analyzing them by sequence analysis (FIGS. 4 & 5).

Example 7

Figure 2:
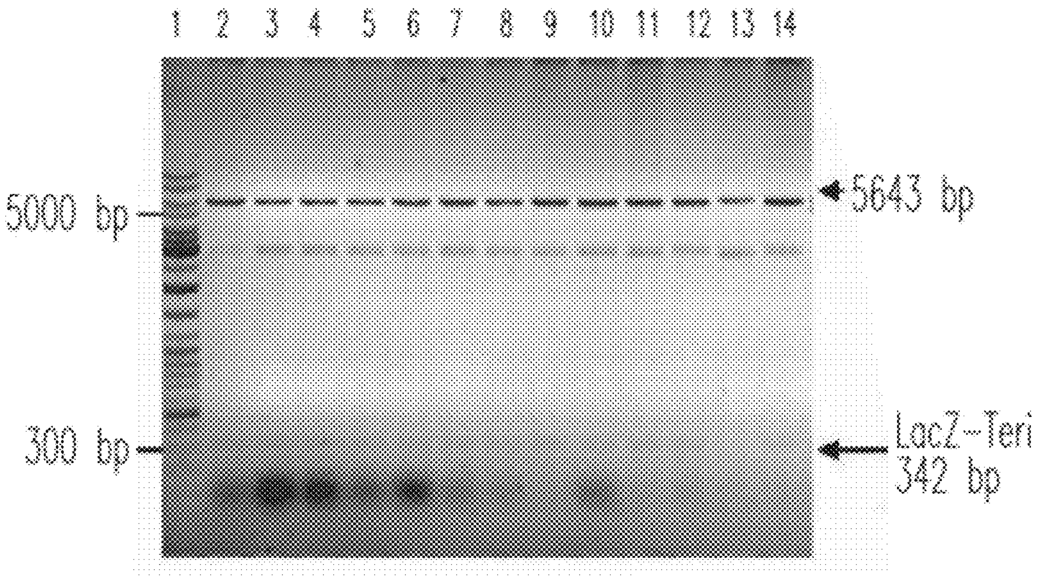

Miniprep DNA of the positive clones were then isolated to purify by following PEG precipitation for sequence analysis (FIG. 2). Sequence was confirmed by using respective forward and reverse primers. After sequence confirmation, these clones were then grown overnight at 37° C. and stored at −70° C. About 10 clones were confirmed as positive by sequence analysis. Sequencing was done by using ABI-Prism.

Among 10 clones, based on the expression level confirmation, final clone was chosen for culturing in 1 L fermentor for development of downstream processing.

Example 8

Preparation of Seed Culture

*Escherichia coli* strain BL21 transformed to express rhPTH(1-34) was purified and maintained as glycerol stock. An aliquot of the glycerol stock was streaked on 2.5% YE plate (2.5% yeast extract, 0.5% sodium chloride pH 7.4, with Agar agar 1.5%) containing ampicillin 50 μl/ml and incubated at 37° C. for 24 hours to obtain isolated colonies. A single colony was inoculated in 10 mL of 2.5% YE liquid medium (2.5% yeast extract, 0.5% sodium chloride pH 7.4) with ampicillin 50 micro liter/ml. in falcon tubes and incubated at 37° C. for 8 to 16 hours. 5 mL of the culture from the tube was inoculated into 500 mL conical flask containing 100 ml basal medium. The flask was incubated at 37° C. on a rotary shaker at 200 rpm for 8 hrs.

Example 9

Fed Batch Fermentation

Figure 6:
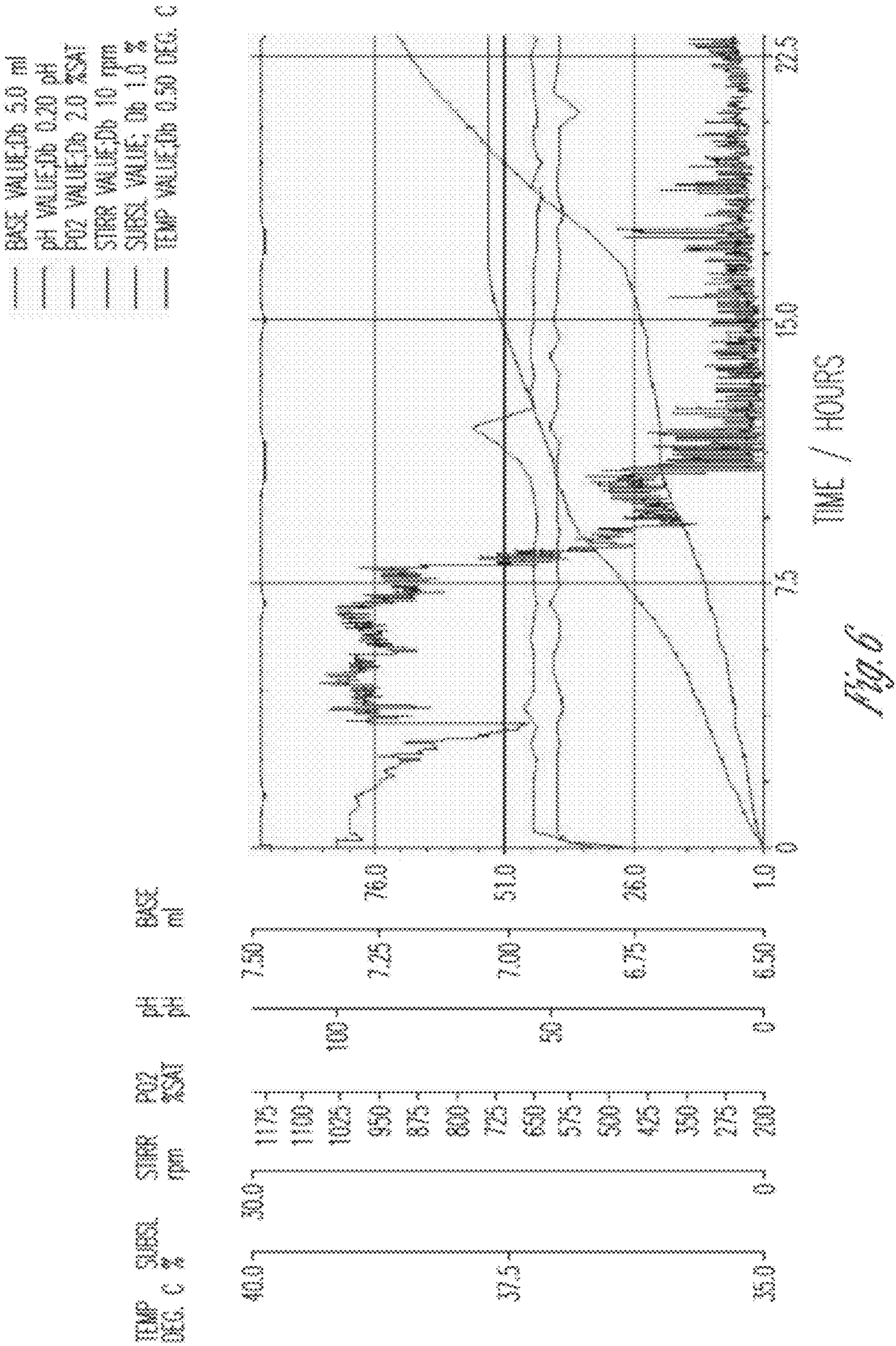
FIG. 6 shows feed and fermentation profile of rhPTH (1-34) clone.
Figure 7:
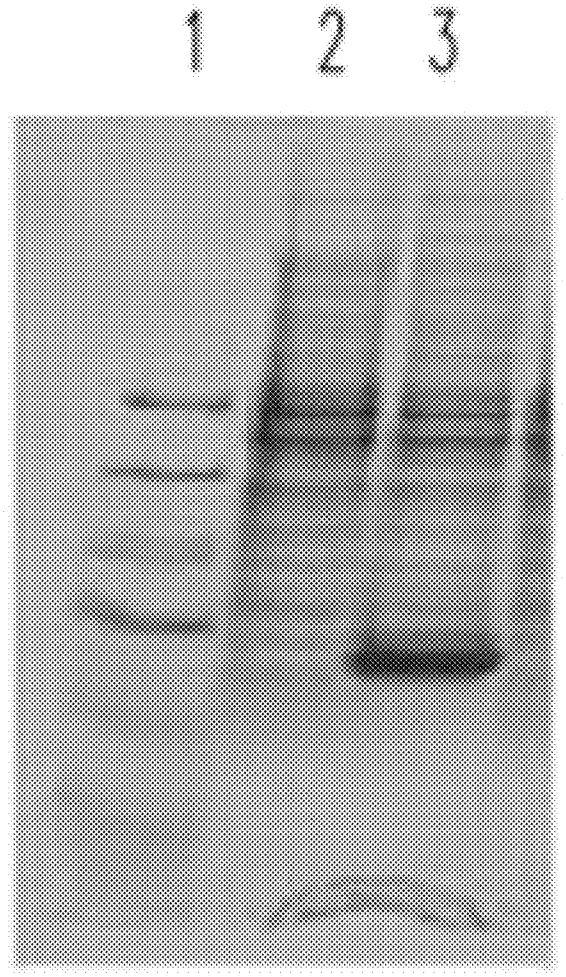
FIG. 7 shows fermentation expression analysis of chimeric rhPTH (1-34). Lane 1: Marker, Lane 2:Uninduced, Lane 3: Induced with lactose.

The above mentioned flask culture was used to inoculate 2 Liter Jar fermenter containing 600 ml of the basal medium. Fermentation was carried out at 37° C. and pH was maintained at 7 using 12.5% of ammonia solution. Stirring was at 1200 rpm with air supply of 10 LPM was maintained throughout the fermentation. The feed medium was pumped to the fermenter following the feed strategy as set in FIG. 6. Induction was carried out at 18 hours from the start of fermentation with 20% solution of Lactose fed at the rate of 0.25 ml/minute. A silicon base antifoam solution was used to control excessive foam. Fermentation was carried out for 24 hours during which samples were taken for measurement of optical density and rhPTH(1-34) production. Yields at different time points were measured by scanning Coomassie blue stained SDS-PAGE gels (Table 1). Analysis of harvested samples from the fermentation broth showed that the average yield of the fusion protein of interest is approximately 3 gms/liter after the first affinity purification. Table 2 gives the feed rate used in the fermentation described in FIG. 7.

TABLE 1

Expression of rhPTH (1-34) in fermenter

| Age of the culture in the fermentor (in hrs) | Optical density at 600 nm | % Yield of rhPTH (1-34) in the total protein |
|---|---|---|
| 0 | 0.36 | 0 |
| 16 | 128.8 | Induction with 20% lactose at 10% constant feed |
| 18 | 141.0 | 10.5 |
| 20 | 125.0 | 10.69 |
| 22 | 102.8 | 15.69 |
| 24 | 108.0 | 13.38 |

TABLE 2

Feed rate used in the fermentation:

| Time | % Feed |
|---|---|
| 0 | 0 |
| 2 | 2 |
| 3.32 | 3 |
| 4.45 | 4 |
| 5.49 | 5 |
| 6.92 | 7 |
| 8.03 | 9 |
| 9.11 | 11 |
| 16.0 | 16 |
| 24 | 16 |

Example 10

Basal Medium Composition

The basal medium, used for the fermentation process contained solutions BS1, BS2, $MgSO_4$ stock solution, Trace element solution (TES) and Antibiotic Stock solution.

BS1 was prepared by dissolving 2.5-15 g of carbon source such as glucose or glycerol and 2.5-15 g nitrogen source such as Yeast extract or Soya peptone in 400-600 ml of RO water.

BS2 was prepared by dissolving 0.5-4 g of ammonium sulphate, 0.8-3.2 g of KH2PO4 and 3.3-13.2 g of $Na_2HPO_4.2H_2O$ and 0.45-1.8 g of sodium chloride in 50-200 ml of RO water.

$MgSO_4$ Stock solution was prepared by dissolving 61.7 g-246.5 g of $MgSO_4.2H_2O$ in 1000 ml of RO water and autoclaved.

TES (Trace element solution) was prepared by dissolving 0.13-1.24 g of $H_3BO_3$, 0.88-0.322 g of $CoCl2.6H_2O$, 0.025-0.1 g of $NaMoO_4.2H_2O$, 0.088-0.352 g of $CaCl_2.2H_2O$, 0.125-0.5 g $MnSO_4.2H_2O$, 2.1-8.35 g $FeCl_3$ and 0.0125-0.05 g $CuSO_4.5H_2O$ and 0.05-0.2 g of $ZnSO_4.7H_2O$ in 500 ml of RO water. The solution was filter sterilized. Antibiotic stock solution consists of filter sterilized ampicillin stock solution (50 mg/ml).

The basal medium was prepared as follows:

400-600 ml of BS1 was mixed with 100-1000 micro liter of antifoam solution (Dow corning 1510 antifoam), prior to autoclaving. To this solution a mixture of 50-200 ml of BS2, 1-5 ml of $MgSO_4$ Stock solution, 1-5 ml of TES and 1-1.5 ml of Antibiotic stock solution are added to form the basal medium. The concentration of carbon source and nitrogen source in the basal medium was between 0.25-1.5 w/v and 0.25-1.5 w/v., respectively.

Example 11

Feed Media Composition

The feed medium, used for the fermentation process contained the solutions, FS1, FS2, FS3 and TES. FS1 was prepared by dissolving 100-200 g of carbon source such as glucose or glycerol in 200-300 ml of RO water. FS2 was prepared by dissolving 100-200 g of nitrogen source such as yeast extract or soya peptone in 250-350 ml of RO water. FS3 was prepared by dissolving 8-10 g of $KH_2PO_4$, 6-9 g of $Na_2HPO_4.2H_2O$ and 6-9 g $K_2HPO_4$ in 25-75 ml of RO water. All above solutions were sterilized by autoclaving. The feed medium was prepared by mixing 200-300 ml of FS1, 250-350 ml of FS2, 25-75 ml of FS3 and 18-25 ml of TES. The concentration of carbon source, nitrogen source and inorganic phosphates in the feed medium was 10-30% w/v and 10-30% w/v and 2.5-4.25% w/v, respectively. The cells obtained after fermentation (carried out as in Example 9) were pelleted and taken for further purification.

Example 12

Cell Clarification, Lysis & Solublisation

Fermentation broth was centrifuged to get cell pellet which was suspended in lysis buffer (50 mM Tris, pH 8.0, 150 mM NaCl) and homogenised. After cooling the homogenised solution to ~10 deg the cells were lysed by pressure disruption at 850 bar and three cycles. To this 8M Urea added and stirred to solublise the proteins. After solublisation the sample (FIG. 7) was filtered through 0.45 um membrane which helped in avoiding channeling in the initial EBA chromatography.

Example 13

Initial Capture of Protein of Interest

The filtered solublised protein solution was loaded on expanded bed of streamline chelating sepharose column after equilibrating the column with buffer A, 20 mM Tris pH 8.0, 150 mm NaCl, 8M Urea and buffer B, 20 mM Tris pH 8.0, 150 mm NaCl, 8M Urea, 250 mM Imidazole.

Figure 8:
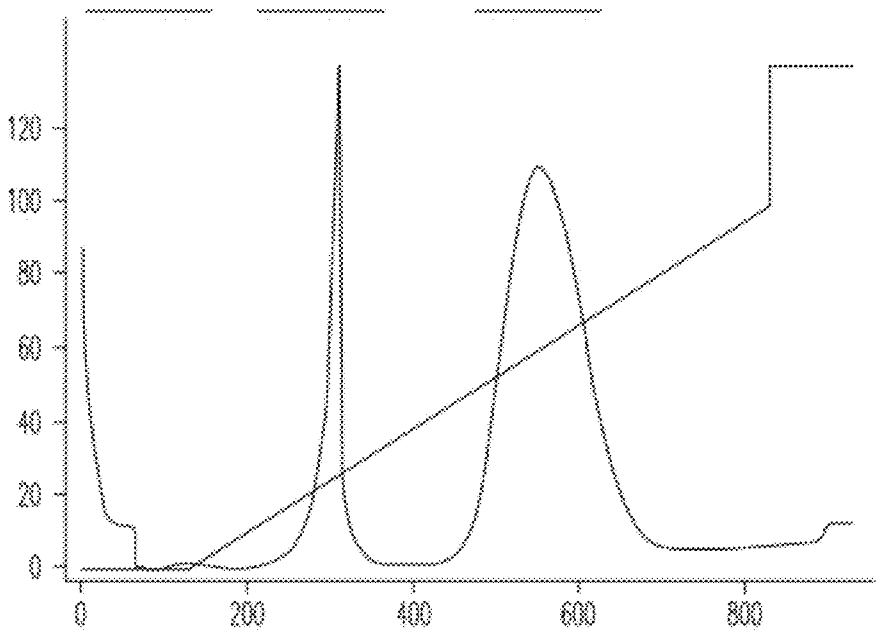
FIG. 8 shows chromatogram of EBA with streamline chelating Sepharose.
Figure 9:
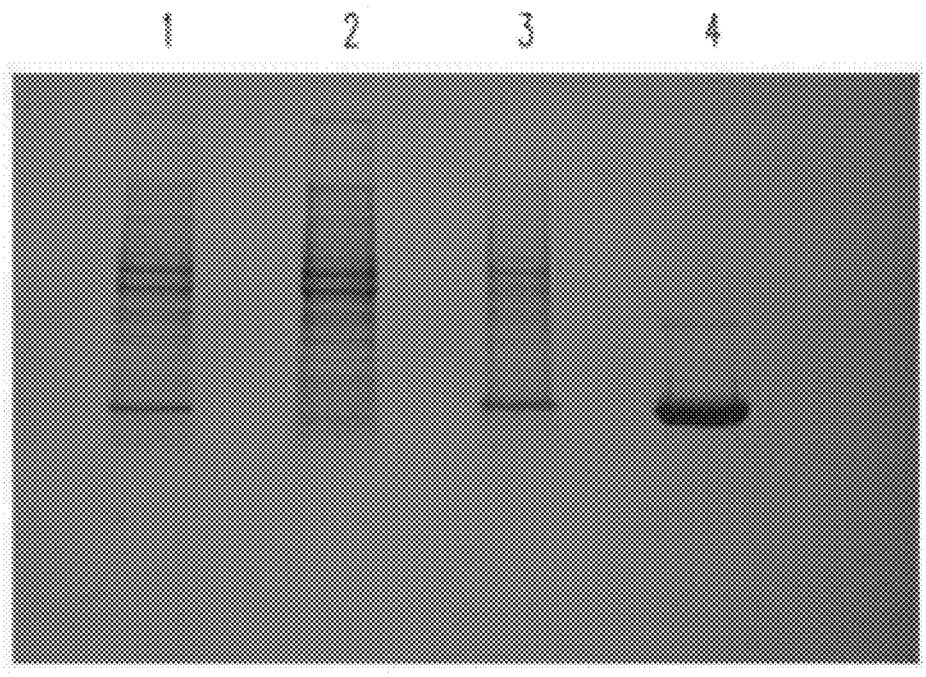
FIG. 9 shows Coomasie stained SDS-PAGE profile of chimeric rhPTH (1-34) using Streamline chelating Sepharose on EBA. Lane 1: Starting material, Lane 2: Unbound (Flow through), Lane 3: Wash, Lane 4: Elution.

After sample loading, the column was washed with buffer A and then the bound protein was eluted with buffer B. The Chromatogram and SDS-PAGE analysis are shown in FIG. 8 and FIG. 9 respectively.

Example 14

Enterokinase Digestion of the Fusion Protein

Figure 10:
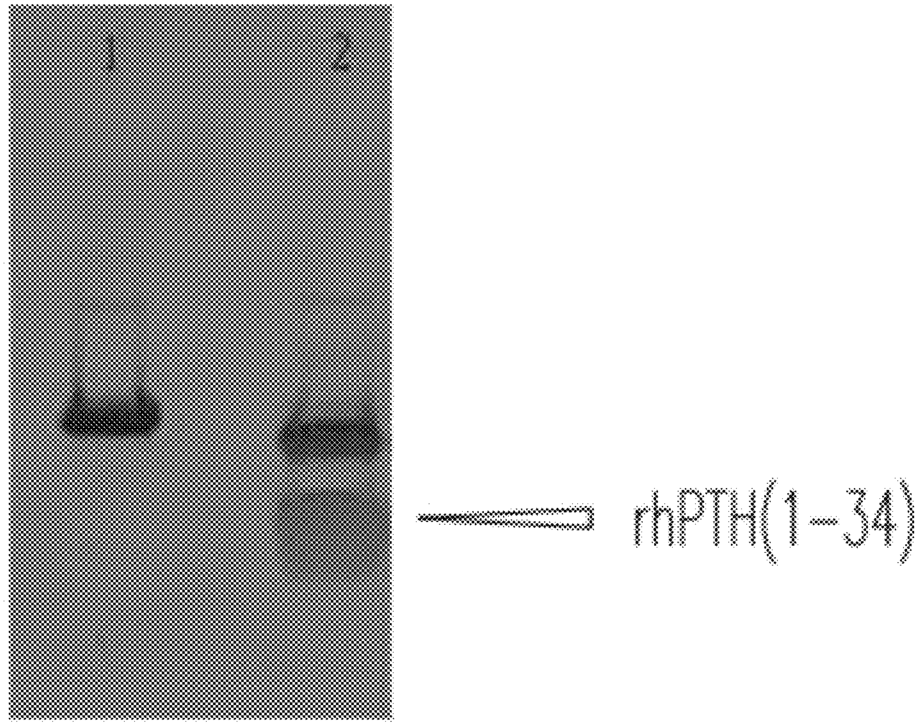
FIG. 10 shows Coomasie stained SDS-PAGE analysis of EK digestion of chimeric rhPTH (1-34). Lane 1:Undigested, Lane 2: EK digested sample.

The EBA elution was diluted with 20 mM Tris pH 8.0 eight times to get a final Urea concentration of ~1M and Enterokinase added at 1:100 (enzyme:substrate) ratio, kept stirring at room temperature for 1 hr. The digested sample was checked on a Tris-Tricine gel shown (FIG. 10).

Example 15

Cation Exchange Chromatography of the Digested Sample

After an hour of EK digestion, the sample pH was adjusted to 7.0 with HCl and then loaded onto a cation exchange column (SP-XL) which was equilibrated with buffer A prior to sample loading. After loading the sample the column was washed with buffer A, 20 mM Sodium acetate pH 5.5 and the bound protein was eluted with a gradient of NaCl in buffer B: 20 mM Sodium acetate pH 5.5, 1M NaCl. The sample pH was adjusted to 7.0 before loading on the column since the charge of the fusion tagged PTH (undigested) and the fusion tag is calculated to be negative and PTH is positively charged and hence only PTH is expected to bind on cation exchanger and similar results were obtained.

Figure 11:
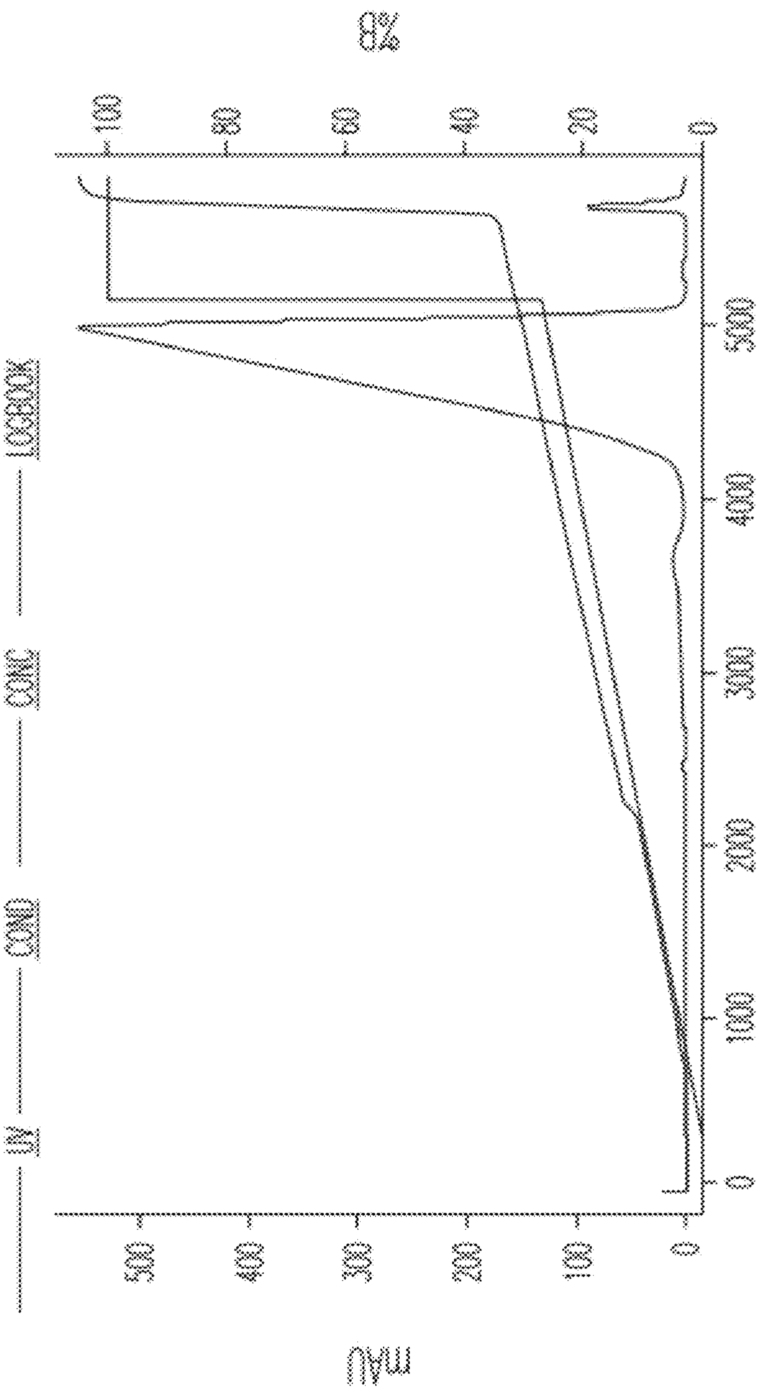
FIG. 11 shows ion exchange chromatogram using SP-XL column.

Cation exchange chromatogram and analysis of the fractions by Tris-Tricine are given (FIG. 11).

Example 16a

Hydrophobic Interaction Chromatography for Final Purification

Figure 12:
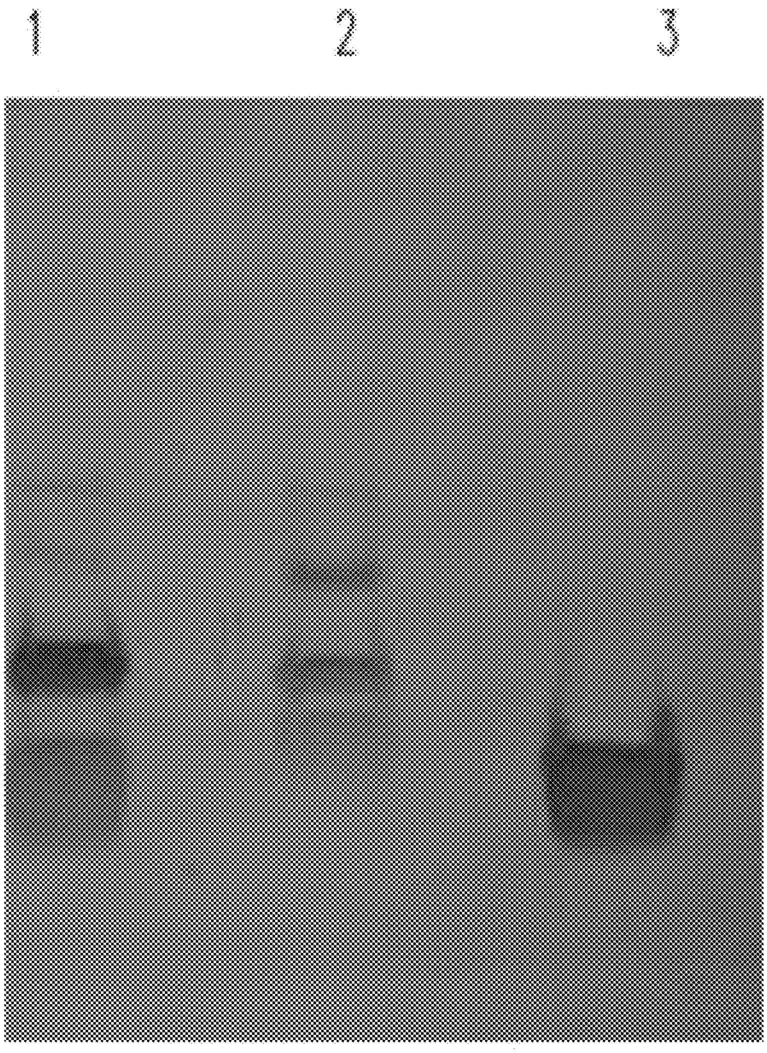
FIG. 12 shows analysis of ion exchange chromatography fractions by gel electrophoresis. Lane 1: Sample loaded on IEX, Lane 2: FT, Lane 3: IEX elution.
Figure 13:
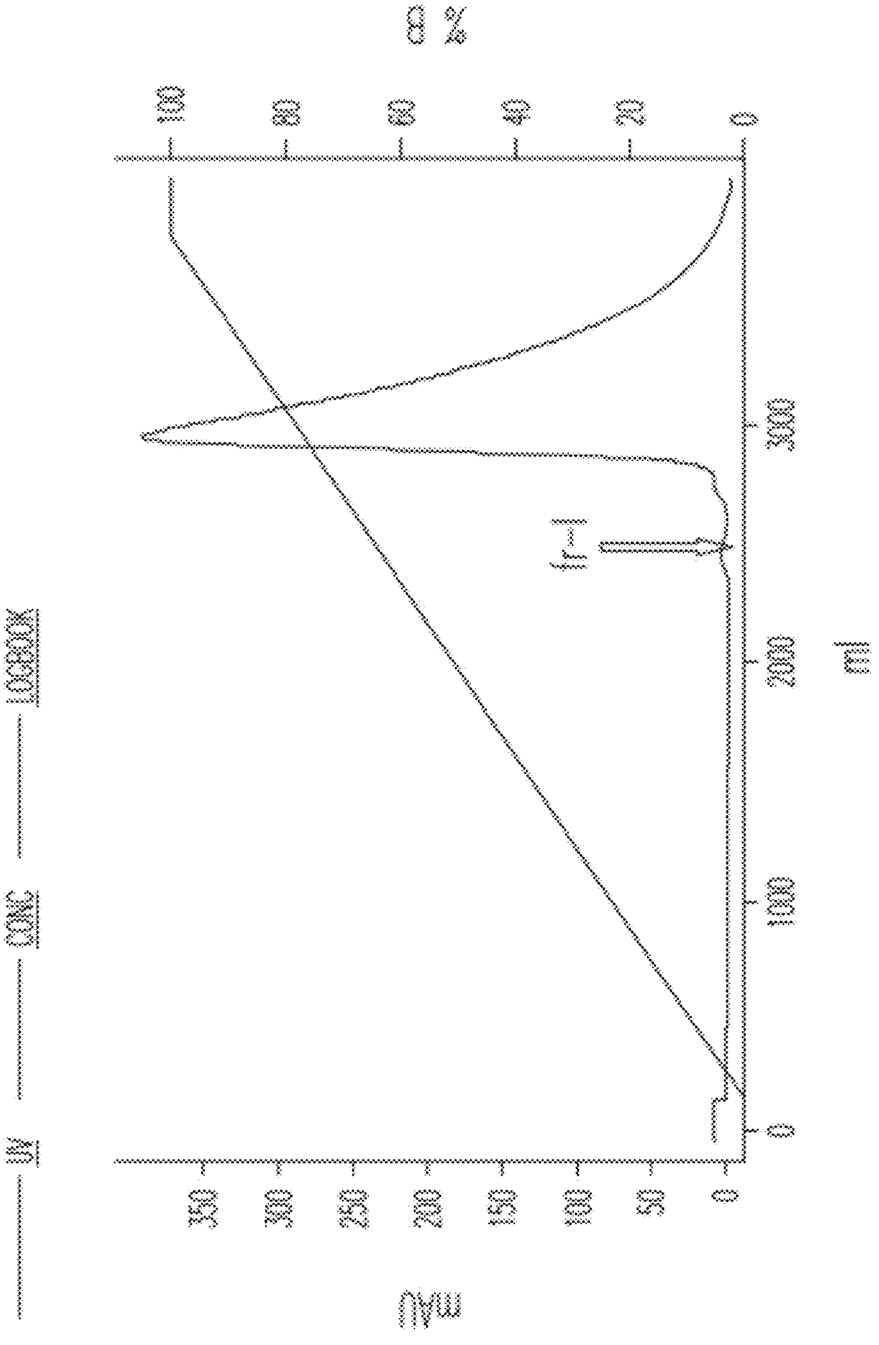
FIG. 13 shows chromatogram of rhPTH (1-34) purification by HIC.
Figure 14:
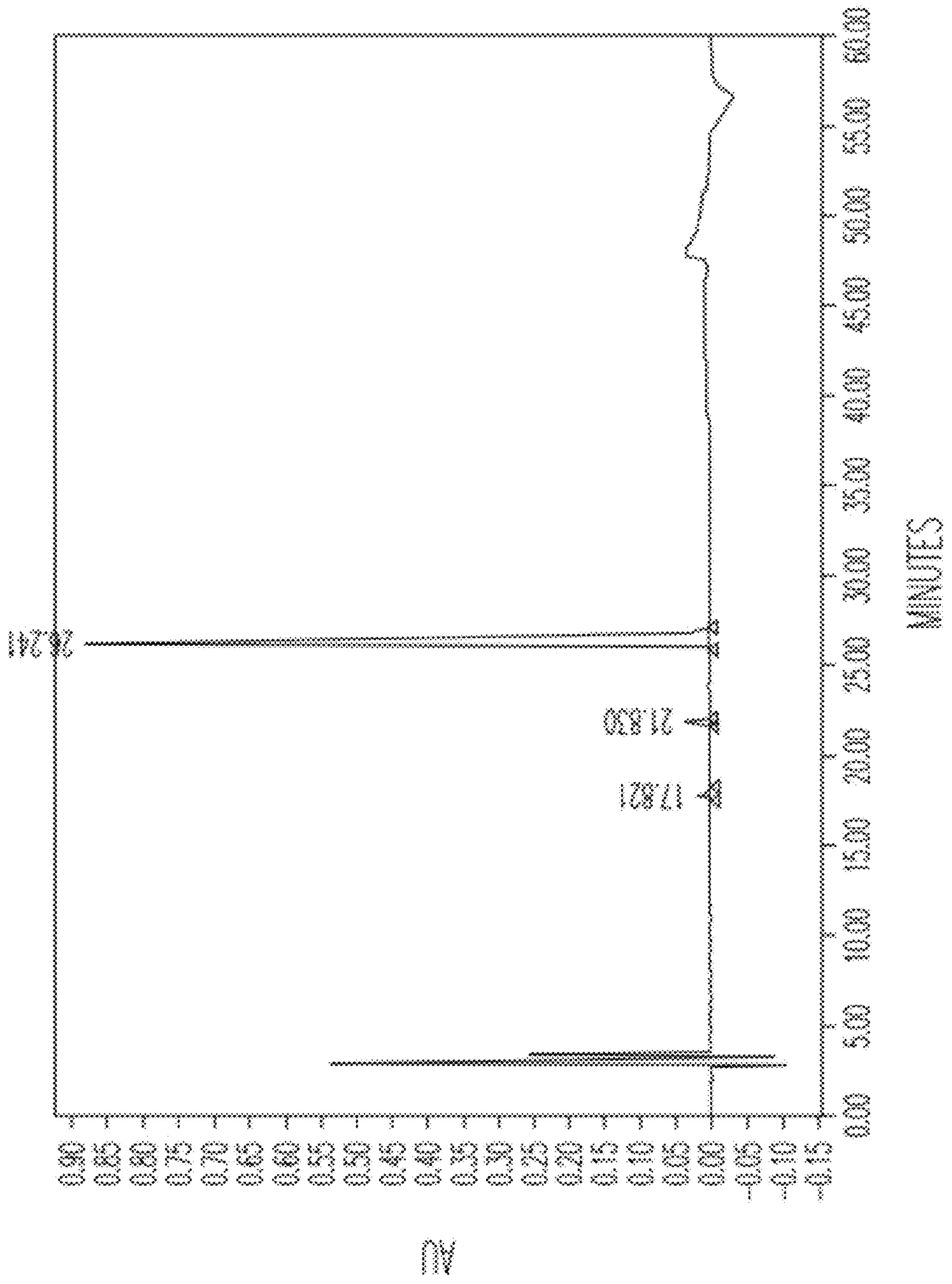
FIG. 14 shows RP-HPLC analysis of fraction 1 of HIC.

To the above IEX elution ammonium sulfate was added to the above IEX elution to a final concentration of 1.75M. After thorough mixing the sample was loaded on Phenyl Sepharose column equilibrated with buffer A, 20 mM Sodium acetate pH 5.5, 1.75M ammonium sulfate, prior to sample loading. After sample loading the column was washed with buffer A and then a gradient elution was done with buffer B, 20 mM Sodium acetate pH 5.5, for final purification. The main peak (see FIG. 12) contains >99% pure PTH(1-34) as anlysed by RP-HPLC. The impurities are eluted just before the main peak as marked in the chromatogram 'fr-1'. Analysis of fr-1 by RP-HPLC is given below (FIG. 14).

Example 16b

Reverse Phase Chromatography for Final Purification

Figure 15:
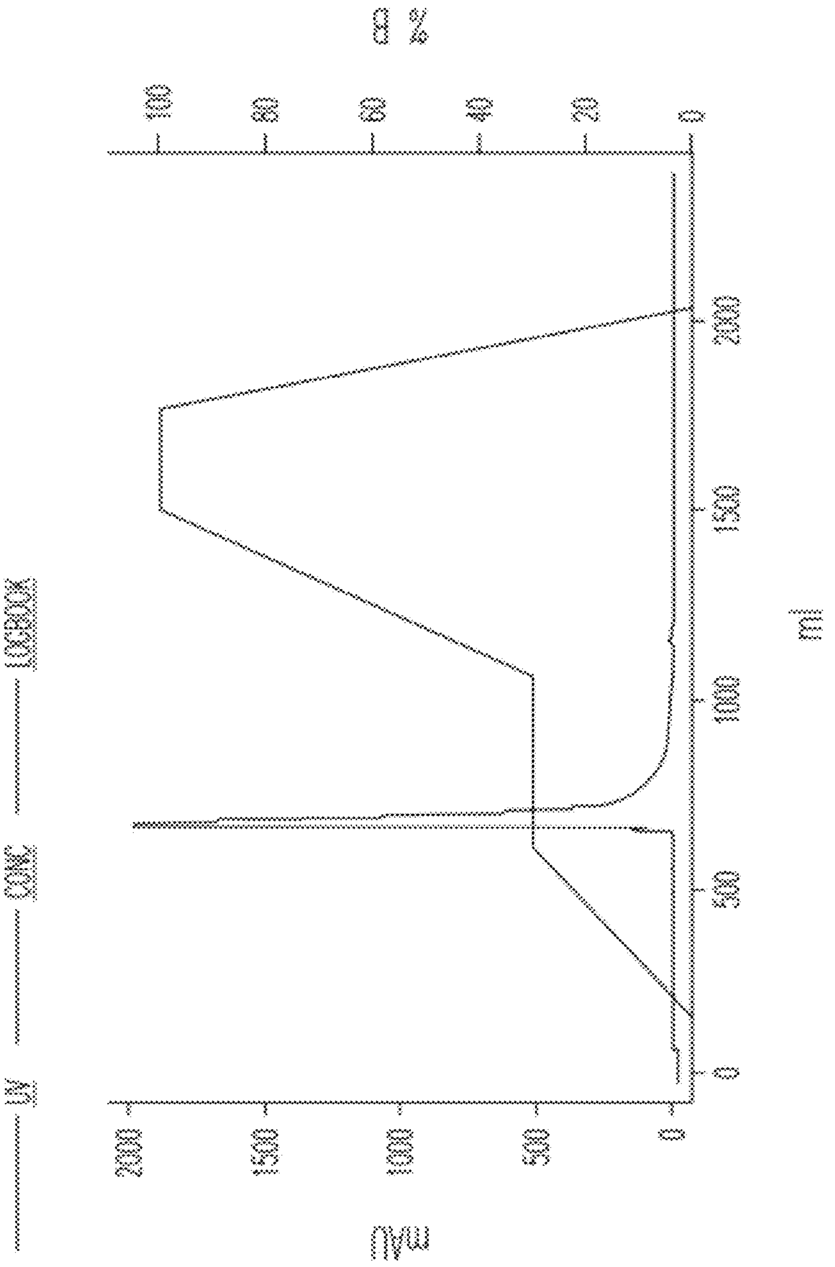
FIG. 15 shows reverse phase chromatographic profile of rhPTH (1-34).

Alternatively final purification of IEX elution was tried using preparative C4 reverse phase silica column. In this method the IEX elution was loaded on the C4 column which was equilibrated with buffer A (0.01% TFA in water). A gradient of upto 30% buffer B (0.1% TFA in 90% Acetonitrile) in 5 Column Volumes (CV) followed by an isocratic at 30% B for 5 CV and then a sharp rise to 100% B in 5CV gave a very good yield of >99% pure PTH(1-34). FIG. 15 shows reverse phase chromatographic purification profile of rhPTH (1-34).

Figure 16:
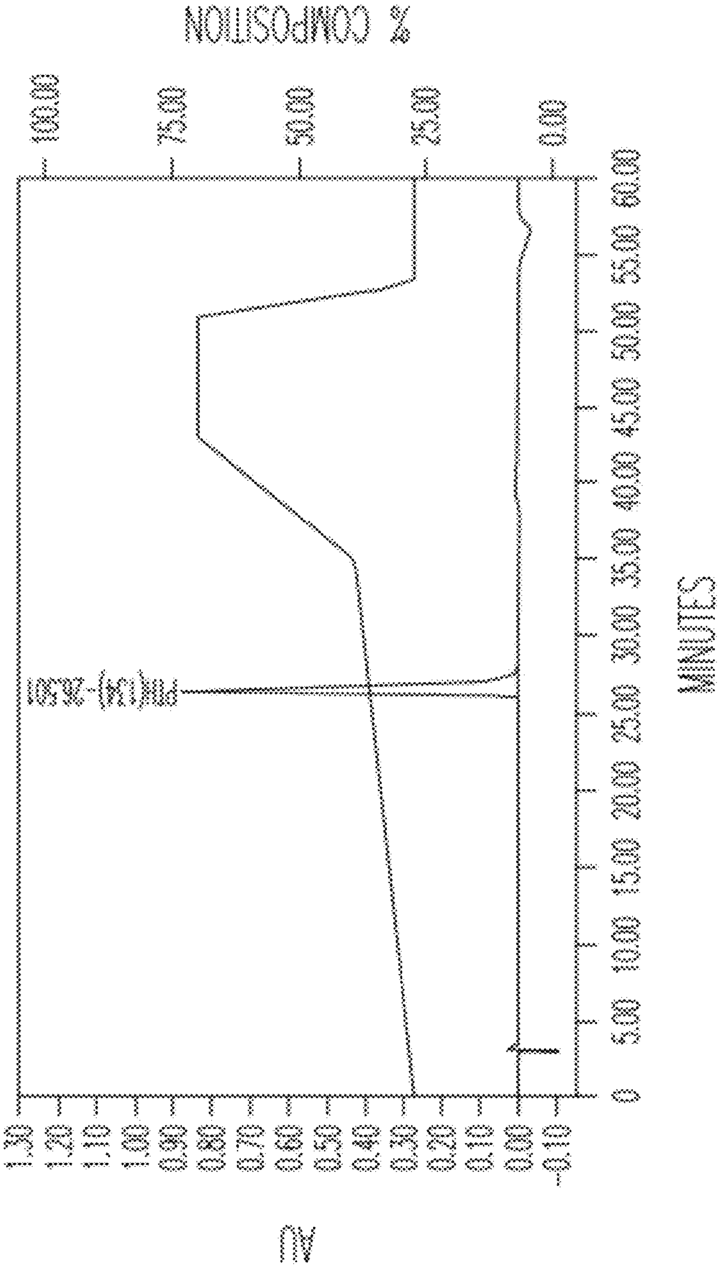
FIG. 16 shows purity analysis of rhPTH (1-34) by RP-HPLC.

Analysis of the final purified PTH(1-34) was done by RP-HPLC using Bachem PTH(1-34) or Forteo as reference and purity confirmed to be >99% consistently (FIG. 16).

PTH(1-34) purified by the above method was analysed by the following methods:

A mass of 4117 Da was obtained by MALDI-TOF.

The first five amino acids from N-terminal sequencing data are Ser Val Ser Glu Iso.

Bioassay using cAMP assay with UMR106 cell line proved our PTH(1-34) to be bioactive.

---

The invention claimed is:

1. A process for synthesis of rhPTH (1-34), said process comprising:

i) constructing a cDNA coding chimeric nucleotide ORF as set forth in SEQ. ID NO.: 1 by amplification of the cDNA by RT-PCR using gene specific primers SEQ. ID NO.: 3, SEQ. ID NO.: 4, SEQ. ID NO.: 5, SEQ. ID NO.: 6, SEQ. ID NO.: 7 and SEQ. ID NO.: 8 encoding rhPTH (1-34) chimeric fusion protein as set forth in SEQ. ID NO.: 2, ii) expressing the chimeric fusion protein in the presence of lactose as inducer in the range of about 10-30% of total protein, iii) purifying the rhPTH (1-34) obtained by an orthogonal process wherein the purification is carried out by cation exchange chromatography to a purity of >98% optionally followed by hydrophobic interaction chromatography (HIC) or RP-HPLC to a purity of ≧99%.

2. The process of claim 1, wherein the synthesis of chimeric nucleotide ORF as set forth in SEQ. ID NO.:1 is under the control of an inducible promoter selected from a group consisting of araBAD, trp, T7, lac, Pho and trc.

3. The process of claim 1, wherein the RP-HPLC column is selected from a group consisting of C4, C8 and C18.

4. The process of claim 2, wherein the promoter is T7.

5. The process of claim 3, wherein the column is C4.

* * * * *

SEQUENCE LISTING

```
<160> NUMBER OF SEQ ID NOS: 11

<210> SEQ ID NO 1
<211> LENGTH: 297
<212> TYPE: DNA
<213> ORGANISM: Homo sapiens

<400> SEQUENCE: 1

atgggcggtg cgcatcatca tcatcatcac gtcgacaatg ttgatgaaag ctggctacag     60

gaaggccaga cgcgaattat ttttgatggc gttaactcgg cgtttcatct gtggattaat    120

gggcgctggg tcggttacgg ccaggacagt cgtttgcccg acgtcggtgc ggtcgacgac    180

gacgacaagt ctgtgagtga aatacagctt atgcataacc tgggaaaaca tctgaactcg    240

atggagagag tagaatggct gcgtaagaag ctgcaggatg tgcacaattt ttaataa       297


<210> SEQ ID NO 2
<211> LENGTH: 97
<212> TYPE: PRT
<213> ORGANISM: Homo sapiens

<400> SEQUENCE: 2
```

-continued

```
Met Gly Gly Ala His His His His His His Val Asp Asn Val Asp Glu
 1               5                  10                  15

Ser Trp Leu Gln Glu Gly Gln Thr Arg Ile Ile Phe Asp Gly Val Asn
            20                  25                  30

Ser Ala Phe His Leu Trp Ile Asn Gly Arg Trp Val Gly Tyr Gly Gln
        35                  40                  45

Asp Ser Arg Leu Pro Asp Val Gly Ala Val Asp Asp Asp Asp Lys Ser
    50                  55                  60

Val Ser Glu Ile Gln Leu Met His Asn Leu Gly Lys His Leu Asn Ser
65                  70                  75                  80

Met Glu Arg Val Glu Trp Leu Arg Lys Lys Leu Gln Asp Val His Asn
                85                  90                  95

Phe
```

<210> SEQ ID NO 3
<211> LENGTH: 31
<212> TYPE: DNA
<213> ORGANISM: Artificial Sequence
<220> FEATURE:
<223> OTHER INFORMATION: A synthetic primer

<400> SEQUENCE: 3
cttttagtga ccatggtacc tgcaaaagac a 31

<210> SEQ ID NO 4
<211> LENGTH: 32
<212> TYPE: DNA
<213> ORGANISM: Artificial Sequence
<220> FEATURE:
<223> OTHER INFORMATION: A synthetic primer

<400> SEQUENCE: 4
tctgttctcg agttcactgg gatttagctt ta 32

<210> SEQ ID NO 5
<211> LENGTH: 30
<212> TYPE: DNA
<213> ORGANISM: Artificial Sequence
<220> FEATURE:
<223> OTHER INFORMATION: A synthetic primer

<400> SEQUENCE: 5
cactataggg gaattgtgag cggataacaa 30

<210> SEQ ID NO 6
<211> LENGTH: 37
<212> TYPE: DNA
<213> ORGANISM: Artificial Sequence
<220> FEATURE:
<223> OTHER INFORMATION: A synthetic primer

<400> SEQUENCE: 6
tatttcactc acagacttgt cgtcgtcgtc gaccgca 37

<210> SEQ ID NO 7
<211> LENGTH: 41
<212> TYPE: DNA
<213> ORGANISM: Artificial Sequence
<220> FEATURE:
<223> OTHER INFORMATION: A synthetic primer

<400> SEQUENCE: 7
gtcgacgacg acgacaagtc tgtgagtgaa atacagctta t 41

-continued

```
<210> SEQ ID NO 8
<211> LENGTH: 45
<212> TYPE: DNA
<213> ORGANISM: Artificial Sequence
<220> FEATURE:
<223> OTHER INFORMATION: A synthetic primer

<400> SEQUENCE: 8

tagaggagct cgaggttatt aaaaattgtg cacatcctgc agctt                    45


<210> SEQ ID NO 9
<211> LENGTH: 5
<212> TYPE: PRT
<213> ORGANISM: Artificial Sequence
<220> FEATURE:
<223> OTHER INFORMATION: A synthetic peptide

<400> SEQUENCE: 9

Ser Val Lys Lys Arg
 1               5


<210> SEQ ID NO 10
<211> LENGTH: 41
<212> TYPE: PRT
<213> ORGANISM: Escherichia coli

<400> SEQUENCE: 10

Val Asp Asn Cys Asp Glu Ser Trp Leu Gln Glu Gly Gln Thr Arg Ile
 1               5                  10                  15

Ile Phe Gly Asp Val Asn Ser Ala Phe His Leu Trp Gly Arg Trp Val
            20                  25                  30

Gly Tyr Gly Gln Asp Ser Arg Leu Pro
        35                  40


<210> SEQ ID NO 11
<211> LENGTH: 4
<212> TYPE: PRT
<213> ORGANISM: Artificial Sequence
<220> FEATURE:
<223> OTHER INFORMATION: A synthetic peptide

<400> SEQUENCE: 11

Asp Asp Asp Lys
 1
```